(12) United States Patent
Chowdhury et al.

(10) Patent No.: US 10,874,341 B2
(45) Date of Patent: Dec. 29, 2020

(54) SYSTEMS AND METHODS FOR DETERMINING NEUROVASCULAR REACTIVITY TO BRAIN STIMULATION

(71) Applicant: Neurotrix LLC, St. Augustine, FL (US)

(72) Inventors: Shubhajit Roy Chowdhury, Kolkata (IN); Anirban Dutta, Kolkata (IN); Abhijit Das, Kolkata (IN)

(73) Assignee: Neurotrix LLC, St. Augustine, FL (US)

( * ) Notice: Subject to any disclaimer, the term of this patent is extended or adjusted under 35 U.S.C. 154(b) by 186 days.

(21) Appl. No.: 15/648,400

(22) Filed: Jul. 12, 2017

(65) Prior Publication Data

US 2017/0340260 A1 Nov. 30, 2017

Related U.S. Application Data

(63) Continuation of application No. PCT/US2016/013476, filed on Jan. 14, 2016.
(Continued)

(30) Foreign Application Priority Data

Jan. 14, 2015 (IN) ............................ 49/KOL/2015

(51) Int. Cl.
*A61B 5/00* (2006.01)
*A61B 5/1455* (2006.01)
(Continued)

(52) U.S. Cl.
CPC .......... *A61B 5/4064* (2013.01); *A61B 5/0075* (2013.01); *A61B 5/0484* (2013.01);
(Continued)

(58) Field of Classification Search
CPC ... A61B 5/4064; A61B 5/1455; A61B 5/6803; A61B 5/0484; A61B 5/14551;
(Continued)

(56) References Cited

U.S. PATENT DOCUMENTS 5,807,270 A 9/1998 Williams
8,140,150 B2 3/2012 Greene et al.
(Continued)

FOREIGN PATENT DOCUMENTS

WO WO-2010127044 A1 11/2010
WO WO-2013173875 A1 11/2013
WO WO-2016115392 A1 7/2016

OTHER PUBLICATIONS

Anirban, et al. (2013) A neural mass model for simulating modulation of cortical activity with transcranial direct current stimulation.
(Continued)

*Primary Examiner* — Eric F Winakur
*Assistant Examiner* — Abid A Mustansir
(74) *Attorney, Agent, or Firm* — Wilson Sonsini Goodrich & Rosati

(57) ABSTRACT

System and methods for stimulating the neurovascular system of the cerebral tissue through optimally placed devices, while simultaneously measuring the evoked neuronal and hemodynamic responses, also using optimally placed devices, is disclosed. Systems and methods for iteratively stimulating the neurovascular system and recording neuronal and hemodynamic responses are also disclosed. Further, a method for determining cerebral neurovascular functioning from the combined stimulation and measurement is disclosed, for use in diagnosis of neurovascular disorders.

21 Claims, 9 Drawing Sheets

Related U.S. Application Data

(60) Provisional application No. 62/204,232, filed on Aug. 12, 2015.

(51) Int. Cl.
*A61N 1/36* (2006.01)
*A61N 1/20* (2006.01)
*A61B 5/0484* (2006.01)
*A61B 5/0476* (2006.01)

(52) U.S. Cl.
CPC ........ *A61B 5/1455* (2013.01); *A61B 5/14551* (2013.01); *A61B 5/6803* (2013.01); *A61N 1/20* (2013.01); *A61N 1/36014* (2013.01); *A61N 1/36025* (2013.01); *A61B 5/0476* (2013.01); *A61B 5/6814* (2013.01)

(58) Field of Classification Search
CPC ... A61B 5/0075; A61B 5/6814; A61B 5/0476; A61N 1/36025; A61N 1/20; A61N 1/36014
See application file for complete search history.

(56) References Cited

U.S. PATENT DOCUMENTS

| | | | |
|---|---|---|---|
| 8,239,030 | B1 | 8/2012 | Hagedorn et al. |
| 8,396,557 | B2 | 3/2013 | Dilorenzo et al. |
| 9,326,725 | B2* | 5/2016 | Finkel .................. A61B 5/0484 |
| 2004/0049105 | A1 | 3/2004 | Crutchfield et al. |
| 2004/0122281 | A1 | 6/2004 | Fischell et al. |
| 2007/0088403 | A1 | 4/2007 | Wyler et al. |
| 2013/0225953 | A1* | 8/2013 | Oliviero ............... A61N 1/0408 600/323 |
| 2013/0345774 | A1* | 12/2013 | Paulus .................. A61N 1/323 607/45 |
| 2017/0202476 | A1* | 7/2017 | Desain ................. A61B 5/7246 |

OTHER PUBLICATIONS

Attwell, et al. (2010). Glial and neuronal control of brain blood flow. Nature 468: 232-243.
Bale, et al. (2014). A new broadband near-infrared spectroscopy system for in-vivo measurements of cerebral cytochrome-c-oxidase changes in neonatal brain injury. Biomed Opt Express 5: 3450-3466.
Behzadi, et al. (2005) An arteriolar compliance model of the cerebral blood flow response to neural stimulus. Neuroimage 25(4): 1100-1111.
Boas, et al. (2003). Can the cerebral metabolic rate of oxygen be estimated with near-infrared spectroscopy? Phys Med Biol. 48: 2405-2418.
Buxton, et al. (1997). A model for the coupling between cerebral blood flow and oxygen metabolism during neural stimulation. J Cereb Blood Flow Metab Off J Int Soc Cereb Blood Flow Metab. 17: 64-72.
Buzsaki, et al. (2012) The origin of extracellular fields and currents-BEG, ECoG, LFP and spikes. Nat Rev Neurosci. 13(6): 407-420.
David, et al. (2003) A neural mass model for MEG/EEG: coupling and neuronal dynamics. Neuroimage 20: 1743-1755.
Dhamala, et al. (2008) Analyzing information flow in brain networks with nonparametric Granger causality. Neuroimage 41: 354-362.
Dutta, A. (2015) Bidirectional interactions between neuronal and hemodynamic responses to transcranial direct current stimulation (tDCS): challenges for brain-state dependent tDCS. Front Syst Neurosci, 10:9, 107.
Dutta. Electroencephalography (EEG)-near-infrared spectroscopy (NIRS) based online imaging during non-invasive electrical brain simulation. Engineering Science [physics]. 2014.<hal-01100751>.
Dutta, et al. (2013). A phenomenological model for capturing cerebrovascular reactivity to anodal transcranial direct current stimulation. In: 2013 6th Int. IEEEEMBS Conf. Neural Eng. NER. 827-830.
Dutta, et al. (2013). Neural mass model analysis of online modulation of electroencephalogram with transcranial direct current stimulation. In: 2013 6th Int. IEEEE MBS Conf. Neural Eng. NER. 206-210.
EP16737911.4 Extended European Search Report dated Sep. 7, 2018.
Flitney, et al. (2003). Nitric oxide and the mechanism of rat vascular smooth muscle photorelaxation. J Physiol. 550: 819-828.
Friston, et al. (2000). Nonlinear responses in fMRI: the Balloon model, Volterra kernels, and other hemodynamics. Neuroimage 12: 466-477.
Friston, et al. (2007). Variational free energy and the Laplace approximation. Neuroimage 34: 220-234.
Friston, et al. (2008). Multiple sparse priors for the M/EEG inverse problem. Neuroimage 39: 1104-1120.
Giovannella, et al. Concurrent measurement of cerebral hemodynamics and electroencephalography during transcranial direct current stimulation. Neurophotonics, 5(1), 015001 (2018). doi:10.1117/1.NPh.5.1.015001.
Girouard, et al. (2006). Neurovascular coupling in the normal brain and in hypertension, stroke, and Alzheimer disease. J Appl Physiol Bethesda Md 1985, 100: 328-335.
Gonzalez-Lima, et al. (2014). Augmentation of cognitive brain functions with transcranial lasers. Front Syst Neurosci. 8:36. 10.3389/fnsys.2014.00036.
Huang, et al. ( 1998) The empirical mode decomposition and the Hilbert spectrum for nonlinear and non-stationary time series analysis. Proc R Soc Lond Ser Math Phys Eng Sci. 454: 903-995.
Huneau, et al. (2015). Investigating Human Neurovascular Coupling Using Functional Neuroimaging: A Critical Review of Dynamic Models. Front Neurosci. 9: 467.
Iadecola. Neurovascular regulation in the normal brain and in Alzheimer's disease. Nature Reviews Neuroscience vol. 5, pp. 347-360 (May 1, 2004).
International search report with written opinion dated Mar. 18, 2016 for PCT/US2016/013476.
Jindal, et al. Development of a low-cost point of care device for near-infrared spectroscopy (NIRS) based online imaging during non-invasive electrical brain simulation. [Research Report] Inria Sophia Antipolis. 2015.< hal-01203366>.
Karu, et al. (1995). [Cytochrome c oxidase as the primary photoacceptor upon laser exposure of cultured cells to visible and near IR-range light]. Dokl Akad Nauk 342(5): 693-695.
Khadka, et al. (2015) Principles of Within Electrode Current Steering!. J Med Devices 9: 020947-020947.
Luby, et al. (2014). Immediate Changes in Stroke Lesion Volumes Post-Thrombolysis Predict Clinical Outcome. Stroke 45(11): 3275-3279. 10.1161/STROKEAHA.114.006082.
Lucas, et al. (2010). Influence of Changes in Blood Pressure on Cerebral Perfusion and Oxygenation. Hypertension 55 (3): 698-705.
Molae-Ardekani, et al. (2013). Effects of transcranial Direct Current Stimulation (tDCS) on cortical activity: A computational modeling study. Brain Stimulat 6: 25-39.
Moore, et al. (2008). The hemo-neural hypothesis: on the role of blood flow in information processing. J Neurophysiol. 99 (5): 2035-2047.
Moran, et al. (2007) A neural mass model of spectral responses in electrophysiology. Neuroimage 37: 706-720.
Nicholson, et al. (1975). Theory of current source-density analysis and determination of conductivity tensor for anuran cerebellum. J Neurophysiol. 38: 356-368.
Ou et al. Study of neurovascular coupling in humans via simultaneous magnetoencephalography and diffuse optical imaging acquisition. Neuroimage 46(3):624-632 (Jul. 1, 2009).
Pulgar, V.M. (2015). Direct electric stimulation to increase cerebrovascular function. Front Syst Neurosci 9:54, 5 pages.
Rahman, et al. (2013). Cellular effects of acute direct current stimulation: somatic and synaptic terminal effects. J Physiol. 591: 2563-2578.

(56) References Cited

OTHER PUBLICATIONS

Scholkmann, et al. (2014). A review on continuous wave functional near-infrared spectroscopy and imaging instrumentation and methodology. Neuroimage 85 Pt 1: 6-27.
Sood. Investigating online effects of transcranial direct current simulation from NIRS-EEG joint-imaging using Kalman Filter based online parameter estimation of an autoregressive model. 2015.
Sotero, et al. (2007) Realistically coupled neural mass models can generate EEG rhythms. Neural Comput 19: 478-512.
Ursino M, et al. (2010) The generation of rhythms within a cortical region: analysis of a neural mass model. Neuroimage 52(3): 1080-1094.
Villringer, et al. (1997). Non-invasive optical spectroscopy and imaging of human brain function. Trends Neurosci 20(10): 435-442.
Whalen, et al. (2015). Observability and Controllability of Nonlinear Networks: The Role of Symmetry. Phys Rev X 5: 011005.
Windhoff, et al. (2013) Electric field calculations in brain stimulation based on finite elements: an optimized processing pipeline for the generation and usage of accurate individual head models. Hum Brain Mapp. 34 (4): 923-935.
Zavagilia, et al. (2006). A neural mass model for the simulation of cortical activity estimated from high resolution EEG during cognitive or motor tasks. J Neurosci Methods 157: 317-329.

\* cited by examiner

SYSTEMS AND METHODS FOR DETERMINING NEUROVASCULAR REACTIVITY TO BRAIN STIMULATION

CROSS REFERENCE TO RELATED APPLICATIONS

This application is a continuation of PCT Application No. PCT/US2016/013476, filed Jan. 14, 2016, which claims the benefit of the priority date of U.S. Provisional Patent Application Ser. No. 62/204,232 titled "Apparatus for Determining Neurovascular Reactivity Through Brain Stimulation By Recordal of Neural and Haemodynamic Responses", filed Aug. 12, 2015, by Shubbajit Roy Chowdury, Anirban Dutta, and Abhijit Das; which claims the benefit of the priority date of Indian Patent Application No. 49/KOL/2015, titled "Apparatus for Determining Neurovascular Reactivity Through Brain Stimulation By Recordal of Neural and Haemodynamic Responses", filed Jan. 14, 2015, by Shubhajit Roy Chowdhury, Anirban Dutta, and Abhijit Das. The foregoing applications are incorporated herein in their entirety.

FIELD OF THE INVENTION

The present invention relates generally to medical diagnostic systems and methods. More particularly, the invention relates to devices, systems and methods for determining neurovascular reactivity, using stimulation of the neurovascular system and contemporaneous recording of neuronal and hemodynamic response thereto. The invention further relates to methods for determining cerebral neurovascular functioning, using contemporaneous recording of stimulation-evoked neuronal and hemodynamic responses.

BACKGROUND OF THE INVENTION

Stroke is a significant cause of disability and death, and is a growing problem for global healthcare. More than 700,000 people in the United States alone suffer a stroke each year, and of these, more than 150,000 people die. Of those who survive a stroke, roughly 90% will suffer long term impairment of movement, sensation, memory, or reasoning, ranging from mild to severe. The total cost to the U.S. healthcare system is estimated to be over $50 billion per year.

Stroke may be caused from a rupture of a cerebral artery (referred to as a "hemorrhagic stroke"), or by a blockage or occlusion in a cerebral artery resulting from a thromboembolism (referred to as an "ischemic stroke"). Roughly 80% of strokes are classified as ischemic. When a patient experiences an ischemic stroke, the occlusion prevents blood flow to vital brain tissue, thereby depriving the tissue of oxygen, causing nerve cell damage and potentially cell death. In addition to the vessel occlusion, an identifiable ischemic core is formed, as well as a penumbra, which is a region of tissue that is still viable but in which the cells are oxygen deprived, as a result of a gradient of perfusion deficit in the penumbra. The occlusion primarily, but also the ischemic core and penumbra are targeted areas for treatment.

Among patients experiencing a stroke due to a large vessel occlusion, approximately 1.9 million nerve cells (or neurons) are at risk for irreversible injury every minute that elapses, until blood flow is restored. Providing rapid and effective diagnosis and treatment of stroke is therefore vital for protecting and restoring patient health. But despite the fact that stroke is a prevalent cause of disability and death, available methods for diagnosing stroke are limited.

Stroke is typically diagnosed first by utilizing patient interview and examination, including protocol to detect one-sided weakness or paralysis, speech difficulty, or other common symptoms of stroke. Following patient evaluation, diagnostic imaging (such as CT scan, MRI, ultrasound, or some combination thereof) is routinely performed in order to definitively diagnose a stroke. The imaging process is initiated in hopes of determining the location of an occlusion, and preparing clinicians for treating the clot. However, patient evaluation remains very subjective and variable from patient to patient, and there also remain limitations to imaging for accurate diagnosis of stroke. Further, unlike in a case of diagnosis of other common diseases, such as myocardial infarction (or heart attack), there is no equivalent of an electrocardiogram (EKG), and blood tests are not helpful for definitively diagnosing stroke. Therefore, there remains a need for improved systems and methods for diagnosing stroke.

The diagnostic potential of methods utilizing optical radiation (or light), including light in the visible range of the spectrum and near infrared, has long been accepted. Known methods include transmittance measurements of near infrared spectroscopy (NIRS), used to non-invasively monitor blood oxygenation. NIRS may be used in non-invasive methods to monitor cerebral functioning, because brain function is closely related to blood oxygenation, and the hemodynamics that provide glucose through neurovascular coupling. NIRS wavelengths can be selected such that the change in concentration of oxy-hemoglobin (HbO2) and deoxy-hemoglobin (Hb) in the brain tissue can be detected. The scalp, skull, cerebrospinal fluid, and surrounding tissues of the brain present an optical window of tissue transparency within the near-infrared range of the light spectrum which permits diagnostic measurement. The attenuation of light by the tissue is measured and the concentration of oxygenated hemoglobin is calculated via accepted mathematical models.

Non-invasive brain stimulation (NIBS), e.g. direct electrical stimulation [1] and photobiostimulation [2], can be used to perturb the neurovascular state of the cerebral tissue. An example of NIBS, also referred to herein as perturbation energy, is transcranial direct current stimulation (tDCS) is an accepted means of neurostimulation which uses constant, low amplitude current delivered to the brain via electrodes placed selectively on the scalp. Transcranial direct current stimulation (tDCS) has been shown to modulate cortical neural activity. Other forms of energy may serve as perturbation energy within the scope of the invention. During short-duration brain stimulation, neurovascular reactivity (NVR), and consequently cerebral blood flow, can be measured as the change in neuronal activity in conjunction with hemodynamics and changes therein resulting from energy injection through brain stimulation. The neurovascular unit (NVU) referred to herein consists of the endothelium, glia, neurons, pericytes, and the basal lamina, and has been documented to maintain the homeostasis of the brain microenvironment [3]. The changes in hemodynamics referred to herein are the spatiotemporal dynamics in the millisecond-to-second-range direct interaction (such as via diffusible messengers, electromechanical and thermal interactions) and indirect interaction in the seconds-to-tens-of-seconds-range in the NVU following brain stimulation. During neural activity, energy in the form of the electric currents from exitable membranes of brain tissue generate a potential, which is referred to as the electroencephalogram (EEG) when recorded from the scalp. Neuronal and hemodynamic responses can be measured with multi-modal functional neuroimaging, e.g. near-infrared spectroscopy (NIRS) and electroencephalogram (EEG).

It is an object of the invention to present a multi-modal brain stimulation system to differentially stimulate different components of the neurovascular unit (NVU) to facilitate the observability of its state of functioning, including neurovascular uncoupling. It is a further object of the invention to provide a system for stimulating the brain tissue and contemporaneously recording reaction to the stimulation, as evidenced by changes in hemodynamics and changes in electrophysiological signal, both separately and together, entering the recorded data into one or more mathematical models to determine whether there is a deficit in neurovascular functioning in a subject. It is a further object of the invention to abstractly represent the NVU response to energy perturbation in order to determine the functioning of the NVU in various neurovascular disorders.

It is a further object of the invention to provide a portable device enabled to simultaneously stimulate and acquire evoked data representing neuronal and hemodynamic activity. The sensor-stimulator montage of the portable device is initialized optimally based on population data from both healthy subjects and subjects with a specific neurovascular disorder, which can be determined apriori by conducting conventional imaging, for example, magnetic resonance imaging (MRI), CT scan, or other means.

It is a further object of the invention, to provide a process to determine the functioning of the NVU in various neurovascular disorders based on simultaneously acquired brain stimulation-evoked neuronal and hemodynamic responses. In other words, it is an object of the invention to determine neurovascular function of cerebral tissue in a region of interest, including whether a deficit in neurovascular function exists and the location of the source of the neurovascular deficit.

Description of the Background Art

Pulgar V M (2015) Direct electric stimulation to increase cerebrovascular function. Front Syst Neurosci 9:54; Gonzalez-Lima F, Barrett D W (2014) Augmentation of cognitive brain functions with transcranial lasers. Front Syst Neurosci. doi: 10.3389/fnsys.2014.00036; Iadecola C (2004) Neurovascular regulation in the normal brain and in Alzheimer's disease. Nat Rev Neurosci 5:347-360; Girouard H, Iadecola C (2006) Neurovascular coupling in the normal brain and in hypertension, stroke, and Alzheimer disease. J Appl Physiol Bethesda Md. 1985 100:328-335; Attwell D, Buchan A M, Charpak S, Lauritzen M, Macvicar B A, Newman B A (2010) Glial and neuronal control of brain blood flow. Nature 468:232-243; Lucas S J E, Tzeng Y C, Galvin S D, Thomas K N, Ogoh S, Ainslie P N (2010) Influence of Changes in Blood Pressure on Cerebral Perfusion and Oxygenation. Hypertension 55:698-705; Moore C I, Cao R (2008) The hemo-neural hypothesis: on the role of blood flow in information processing. J Neurophysiol 99:2035-2047; Huneau C, Benali H, Chabriat H (2015) Investigating Human Neurovascular Coupling Using Functional Neuroimaging: A Critical Review of Dynamic Models. Neuroenergetics Nutr Brain Health 467; Whalen A J, Brennan S N, Sauer T D, Schiff S J (2015) Observability and Controllability of Nonlinear Networks: The Role of Symmetry. Phys Rev X 5:011005; Dutta A (2015) Bidirectional interactions between neuronal and hemodynamic responses to transcranial direct current stimulation (tDCS): challenges for brain-state dependent tDCS. Front Syst Neurosci 107; Khadka N, Truong D Q, Bikson M (2015) Principles of Within Electrode Current Steeringl. J Med Devices 9:020947-020947; Molaee-Ardekani B, Marquez-Ruiz J, Merlet I, Leal-Campanario R, Gruart A, Sanchez-Campusano R, Birot G, Ruffini G, Delgado-Garcia J-M, Wendling F (2013) Effects of transcranial Direct Current Stimulation (tDCS) on cortical activity: A computational modeling study. Brain Stimulat 6:25-39; Dutta A, Nitsche M. (2013) Neural mass model analysis of online modulation of electroencephalogram with transcranial direct current stimulation. In: 2013 6th Int. IEEEEMBS Conf. Neural Eng. NER. pp 206-210; Zavaglia M, Astolfi L, Babiloni F, Ursino M (2006) A neural mass model for the simulation of cortical activity estimated from high resolution EEG during cognitive or motor tasks. J Neurosci Methods 157:317-329; Sotero R C, Trujillo-Barreto N J, Iturria-Medina Y, Carbonell F, Jimenez J C (2007) Realistically coupled neural mass models can generate EEG rhythms Neural Comput 19:478-512; Moran R J, Kiebel S J, Stephan K E, Reilly R B, Daunizeau J, Friston K J (2007) A neural mass model of spectral responses in electrophysiology. NeuroImage 37:706-720; Ursino M, Cona F, Zavaglia M (2010) The generation of rhythms within a cortical region: analysis of a neural mass model. NeuroImage 52:1080-1094; Buzsáki G, Anastassiou C A, Koch C (2012) The origin of extracellular fields and currents-EEG, ECoG, LFP and spikes. Nat Rev Neurosci 13:407-420; David O, Friston K J (2003) A neural mass model for MEG/EEG: coupling and neuronal dynamics NeuroImage 20:1743-1755; Rahman A, Reato D, Arlotti M, Gasca F, Datta A, Parra L C, Bikson M (2013) Cellular effects of acute direct current stimulation: somatic and synaptic terminal effects. J Physiol 591:2563-2578; Windhoff M, Opitz A, Thielscher A (2013) Electric field calculations in brain stimulation based on finite elements: an optimized processing pipeline for the generation and usage of accurate individual head models. Hum Brain Mapp 34:923-935; Friston K J, Mechelli A, Turner R, Price C J (2000) Nonlinear responses in fMRI: the Balloon model, Volterra kernels, and other hemodynamics. NeuroImage 12:466-477; Karu T I, Afanas'eva N I (1995) [Cytochrome c oxidase as the primary photoacceptor upon laser exposure of cultured cells to visible and near IR-range light]. Dokl Akad Nauk Ross Akad Nauk 342:693-695; Flitney F W, Megson I L (2003) Nitric oxide and the mechanism of rat vascular smooth muscle photorelaxation. J Physiol 550:819-828; Behzadi Y, Liu T T (2005) An arteriolar compliance model of the cerebral blood flow response to neural stimulus. NeuroImage 25:1100-1111; Scholkmann F, Kleiser S, Metz A J, Zimmermann R, Mata Pavia J, Wolf U, Wolf M (2014) A review on continuous wave functional near-infrared spectroscopy and imaging instrumentation and methodology. NeuroImage 85 Pt 1:6-27; Villringer A, Chance B (1997) Non-invasive optical spectroscopy and imaging of human brain function. Trends Neurosci 20:435-442; Boas D A, Strangman G, Culver J P, Hoge R D, Jasdzewski G, Poldrack R A, Rosen B R, Mandeville J B (2003) Can the cerebral metabolic rate of oxygen be estimated with near-infrared spectroscopy? Phys Med Biol 48:2405-2418; Buxton R B, Frank L R (1997) A model for the coupling between cerebral blood flow and oxygen metabolism during neural stimulation. J Cereb Blood Flow Metab Off J Int Soc Cereb Blood Flow Metab 17:64-72; Dutta A, Chowdhury S R, Dutta A, Sylaja P N, Guiraud D, Nitsche M. (2013) A phenomological model for capturing cerebrovascular reactivity to anodal transcranial direct current stimulation. In: 2013 6th Int. IEEEEMBS Conf. Neural Eng. NER. pp 827-830; Bale G, Mitra S, Meek J, Robertson N, Tachtsidis I (2014) A new broadband near-infrared spectroscopy system for in-vivo measurements of cerebral cytochrome-c-oxidase changes in neonatal brain injury. Biomed Opt Express 5:3450-3466; Dutta A (2014) EEG-NIRS based low-cost screening and monitoring of cerebral microvessels functionality; Nicholson C, Freeman J A (1975) Theory of current source-density analysis and determination of conductivity tensor for anuran cerebellum. J Neurophysiol 38:356-368; Huang N E, Shen Z, Long S R, Wu M C, Shih H H, Zheng Q, Yen N-C, Tung C C, Liu H H (1998) The empirical mode decomposition and the Hilbert spectrum for nonlinear and non-stationary time series analysis. Proc R Soc Lond Ser Math Phys Eng Sci 454:903-995; Dhamala M, Rangarajan G, Ding M (2008) Analyzing information flow in brain networks with nonparametric Granger causality. NeuroImage 41:354-362; Anirban Dutta M A N (2013) A neural mass model for simulating modulation of cortical activity with transcranial direct current stimulation; Luby M, Warach S J, Nadareishvili Z, Merino J G (2014) Immediate Changes in Stroke Lesion Volumes Post Thrombolysis Predict Clinical Outcome. Stroke J Cereb Circ. doi: 10.1161/STROKEAHA.114.006082; Friston K, Mattout J, Trujillo-Barreto N, Ashburner J, Penny W (2007) Variational free energy and the Laplace approximation. NeuroImage 34:220-234; Friston K, Harrison L, Daunizeau J, Kiebel S, Phillips C, Trujillo-Barreto N, Henson R, Flandin G, Mattout J (2008) Multiple sparse priors for the M/EEG inverse problem, NeuroImage 39:1104-1120

BRIEF DESCRIPTION OF THE DRAWINGS

The features of the present invention, which are believed to be novel, are set forth with particularity in the appended claims. Embodiments of the present invention will hereinafter be described in conjunction with the appended drawings provided to illustrate and not to limit the scope of the claims, wherein like designations denote like elements, and in which:

DETAILED DESCRIPTION OF THE INVENTION

Figure 1:
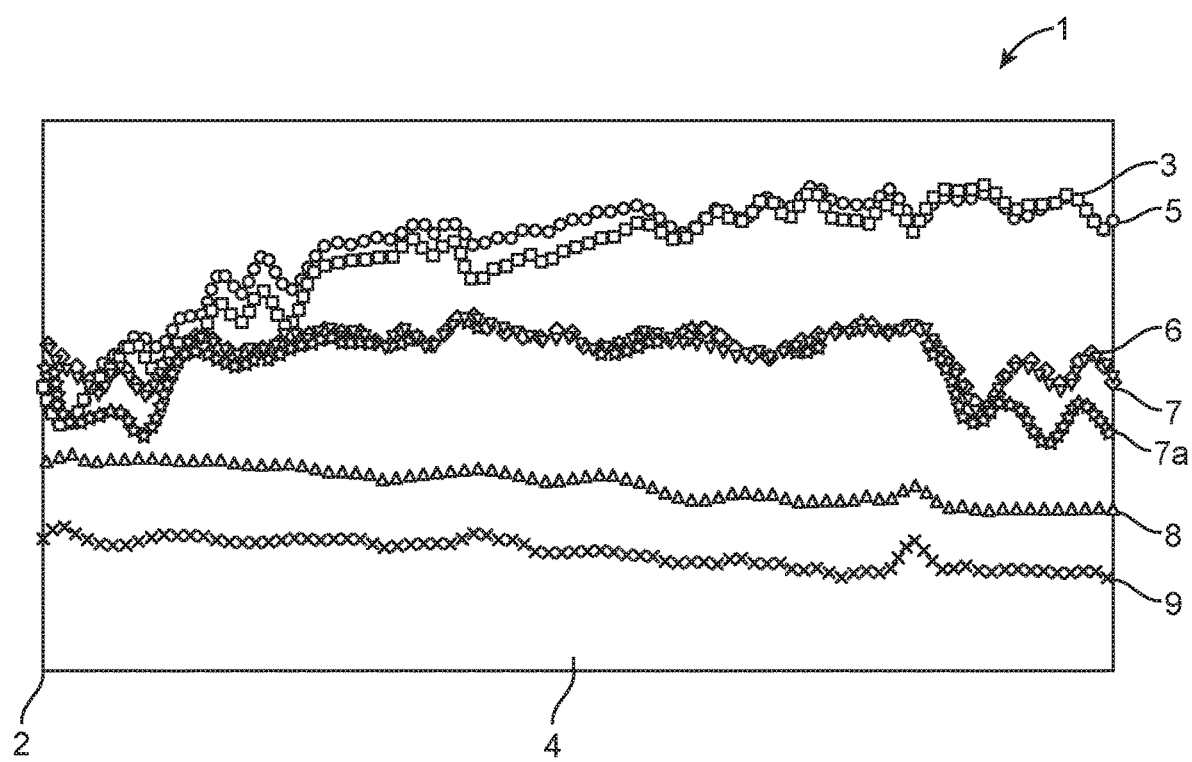
FIG. 1 illustrates the effects of transcranial direct current stimulation (tDCS) with simultaneous recording of electroencephalogram (EEG) and near infrared spectroscopy (NIRS).

As used in the specification and claims, the singular forms "a", "an" and "the" include plural references unless the context clearly dictates otherwise. For example, the term "an article" may include a plurality of articles unless the context clearly dictates otherwise.

Those with ordinary skill in the art will appreciate that the elements in the Figures are illustrated for simplicity and clarity and are not necessarily drawn to scale. For example, the dimensions of some of the elements in the Figures may be exaggerated, relative to other elements, in order to improve the understanding of the present invention.

There may be additional components described in the foregoing application that are not depicted on one of the described drawings. In the event such a component is described, but not depicted in a drawing, the absence of such a drawing should not be considered as an omission of such design from the specification.

It is to be understood that the disclosed device is for exemplary purposes and that this disclosure is not limited to the particular embodiments as described. It is to be understood that the terminology used in this description is for the purposes of describing the exemplary embodiment only and is not intended to limit the scope of the invention. It is apparent from the disclosure that the device can be embodied in a wide variety of forms such that the energy injected as well as the response emanating from the neurovascular substrate actively (evoked response) or passively (baseline response) can take forms other than electrical voltage (such as light, heat, sound, vibration besides others) and the neurovascular substrate can be stimulated with energy other than electrical current (such as light, heat, sound, vibration, besides others). Accordingly, the components and the method steps have been represented, showing only specific details that are pertinent for an understanding of the present invention so as not to obscure the disclosure with details that will be readily apparent to those with ordinary skill in the art having the benefit of the description herein.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

As used herein, the term "subject", "person", "survivors" or "patient" refers to any human, including a healthy human, a human diagnosed with or at risk of a neurovascular deficit, a human being monitored for or undergoing treatment for neurovascular deficit, or a human whose neurovascular deficit status is being assessed or monitored for any reason. These terms are interchangeably used in the present disclosure.

Referring now to a detailed description of the invention, multi-modal non-invasive brain stimulation (NIBS), e.g. direct electrical stimulation and photobiostimulation, can be used to perturb the neurovascular state of the cerebral tissue, for diagnosing the neurovascular functioning, via analysis of the evoked responses. The term neurovascular function is used herein to refer to the bidirectional interactions of blood flow and neuronal activity, as a result of the blood vessels supplying oxygen to neuronal cells, and the neuronal tissues influencing the functioning of the blood vessels via metabolic signals, both culminating in the ability of the vasculature to deliver adequate oxygenated blood and glucose to neural tissue. Neurovascular function is herein assessed on the basis of the bidirectional interactions between the changes in the neuronal activity and/or the alterations in the level of oxygenation of the cerebral tissue in response to the perturbation by NIBS. Here, the neurovascular unit (NVU)

consists of the endothelium, glia, neurons, pericytes, and the basal lamina, the unit that has been proposed as maintaining the homeostasis of the brain microenvironment. Neuronal activity has been shown to be closely related, spatially and temporally, to hemodynamics that supplies glucose via neurovascular coupling [4].

The homeostatic regulation of neuronal activity and hemodynamics and its spatiotemporal dynamics may be probed with short-duration brain stimulation, in order to observe the system response. Here, hemodynamics is altered in brain regions with altered neuronal activity via metabolic coupling mechanisms [5], while cerebral autoregulation mechanisms ensure that the blood flow is maintained during changes of perfusion pressure [6]. During such a short-duration brain stimulation, neurovascular reactivity (NVR) can be measured as the change in neuronal activity, taken alone or in conjunction with hemodynamics in relation to energy injection through brain stimulation. Here, the changes are the spatiotemporal dynamics of the millisecond-to-second-range direct interaction (diffusible messengers, electromechanical and thermal interactions) and seconds-to-tens-of-seconds-range indirect interaction in the NVU following brain stimulation [7]. Here, neuronal and hemodynamic responses measured with multi-modal functional neuroimaging [8], e.g. near-infrared spectroscopy (NIRS) and electroencephalogram (EEG), can be represented abstractly as the system response of the NVU to energy perturbation, e.g. with transcranial direct current stimulation (tDCS) (see FIG. 1). FIG. 1 illustrates the effects of transcranial direct current stimulation (tDCS) with simultaneous recording of electroencephalogram (EEG) and near infra-red spectroscopy (NIRS).

FIG. 1 illustrates the effects of transcranial direct current stimulation (tDCS) with simultaneous recording of electroencephalogram (EEG) and near infrared spectroscopy (NIRS). Plotted on spectrum 1 are the results of multi-modal, non-invasive brain stimulation, by direct electrical current, that has been performed on an experimental model. The differences in plot lines from the start of tDCS 2, to the end of tDCS 4 and beyond for oxygenated hemoglobin (HbO2) and non-oxygenated hemoglobin (HHb), are readily observable in FIG. 1. The EEG and NIRS signals are normalized prior to the start of delivery of tDCS 2. For example, a short distance channel NIRS recording for HbO2 is reflected in plot line 5. In contrast, a short distance channel NIRS recording for HHb is reflected in plot line 9. As an additional example, a long distance channel NIRS recording for HbO2 is reflected in plot line 3. But in contrast, a long distance channel NIRS recording of HHb produces plot line 8. Consequently, the hemodynamic reactivity of cerebral tissue to brain stimulation can readily be compared by comparing the response curves of HbO2 and HHb where adequate blood supply (functional hyperemia) will cause an increase in HbO2 (and decrease in HHb) while a reduced blood supply possibly due to vessel occlusion will cause a decrease in HbO2 (and increase in HHb). Here, simultaneously recorded EEG changes, reflected in plot lines 6, 7, 7a, (and a fourth plot line not visible) provide neuronal reactivity to brain stimulation where EEG power spectrum is known to be closely tied to cerebral blood flow (CBF). As CBF declines, the EEG first loses faster frequencies and then slower frequencies gradually increase. Therefore, EEG provides complimentary information on the state of neuronal functioning where at ischemic threshold the neurons begin to lose their transmembrane gradients leading to cell death (infarction). From this simultaneously acquired neuronal and hemodynamic reactivity data (together called neurovascular reactivity), an estimate of the functioning of the NVU can be made using mathematical model fitted to capture the transfer function between hemodynamic reactivity and neuronal reactivity to brain stimulation. A system and method according to the invention described below in relation to FIGS. 3 and 4 will produce a spectrum such as that illustrated in FIG. 1.

Figure 2:
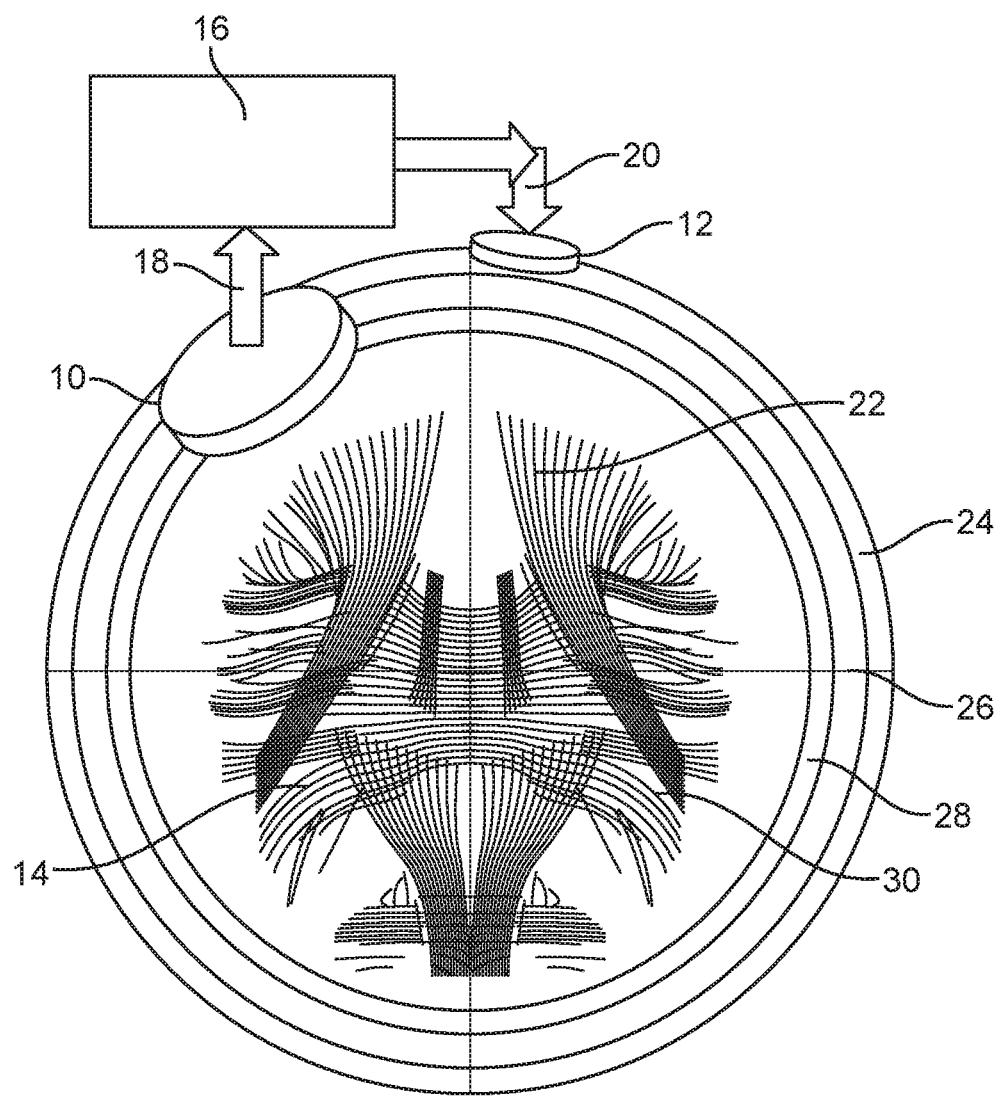
FIG. 2 is a frontal cross sectional view of an embodiment according to the invention.

FIG. 2 shows an embodiment according to the invention mounted on an experimental model. The embodiment of FIG. 2 is a portable system enabled to simultaneously stimulate and acquire evoked data representing neuronal and hemodynamic activity. The devices are shown mounted on a frontal cross-sectional view of a 3-dimensional multi-shell neurovascular head-model to simulate expected healthy brain stimulation-evoked neuronal and hemodynamic activity.

In the embodiment of FIG. 2, recording sensor 10 and stimulation electrode 12 are mounted to neurovascular head model 14. Stimulation electrode 12 can be activated to stimulate neurovascular substrate of head model 14, and recording sensor 10 can be activated to record the results of the stimulation. Recording sensor 10 measures emanating energy 18, which is emanating from the neurovascular substrate as a result of the stimulation. Recording sensor 10 and stimulation electrode 12 are each linked to Data Acquisition and Data Processing (ADADP) unit 16. The measurement of energy 18 is recorded and transmitted to ADADP unit 16 for analysis and processing.

In use, a region of interest (ROI) is identified by the clinician, and likely suspected of functional deficit. ADADP unit 16 directs injected energy 20 into neurovascular head model 14, via stimulation electrode 12. The clinician may steer or direct energy 20 to target a ROI such as cerebral neurovascular substrate 22, and analyze the evoked emanating energy 18 captured by the recording sensor 10, to detect deficit or abnormality, if any.

ADADP unit 16 described in the present invention, in whole or in part, can be implemented on a computer system or network. As will be described in greater detail below, ADADP unit 16 incorporates memory, data acquisition, and data processing to achieve the objectives of the invention. If the ADADP unit 16 detects an abnormality/deficit, it then focuses on the 3D source of the deficit by coordinating the location of injected energy 20 with stimulation electrode 12, and the locations for the response, or emanating energy 18, captured by recording sensor 10, as described in greater detail below. A clinician initially targets a region of interest based upon patient evaluation. For example, if the patient is experiencing difficulties with speech, the clinician will target regions of the brain responsible for speech. As another example, if the patient is exhibiting left sided muscle weakness, the physician will target the hemisphere of the brain responsible for left sided movement. After the clinician initiates the method targeting ROI, such as neurovascular substrate 22, the configuration of recording sensor 10 and stimulation electrode 12 is iteratively changed via the processing functions of ADADP 16 to get a better estimate of the 3D source of deficit.

The optimal scalp locations for energy injection and response recordings, and therefore for recording sensor 10 and stimulation electrode 12, for obtaining a better estimate of the 3D source of deficit are determined based on calculations run on a 3-dimensional multi-shell generative neurovascular head-model, based on a priori population imaging data of both healthy and pathological subjects. The presence of symmetry in the nonlinear network of NVU may challenge observability [9]. Since no real-world network has exact symmetries, optimal placement of sensors and stimulators, along with system identification and parameter estimation techniques [10], will make it possible to determine the functioning of the NVU in various neurovascular disorders. In the example of FIG. 2, neurovascular head model 14 includes scalp 24, skull 26, cerebrospinal fluid 28, and cerebral neurovascular substrate 30. An a priori population imaging data library may be created based on both healthy and pathological subjects, and electric field and photon propagation calculations for electrical and optical stimulation of substrate 30 may be made and compared with the data library. From this data library, initial and adjusted optimal scalp locations for initiation of energy injection and recording can be determined. It will be understood that in the foregoing example, an electrode or sensor may in reality be comprised of an array of electrodes or sensors, and that injected, absorbed, or emanating energy may be in any of a variety of forms, such as electricity, light, sound, heat, or other form.

Figure 3:
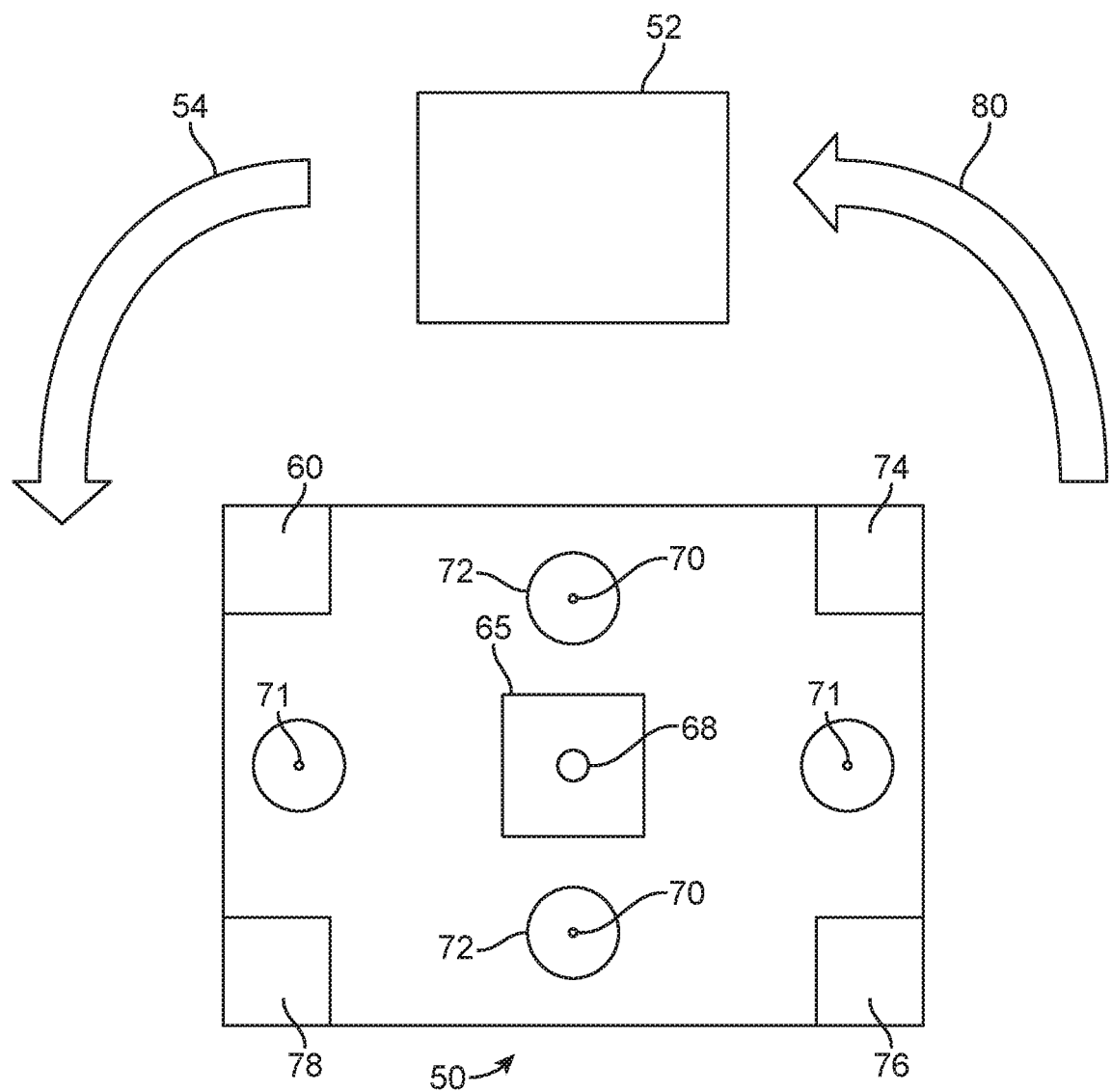
FIG. 3 is a schematic illustration of a component of an alternative embodiment according to the invention.

Turning now to FIG. 3, a component of an alternative embodiment according to the invention is illustrated. Single sensor-stimulator unit 50 performs the functions of the separate recording sensor and stimulating electrode described above in relation to FIG. 2. One or more sensor-stimulator units 50 may be selectively placed at optimal scalp locations as discussed above. In the embodiment of FIG. 3, sensor-stimulator unit 50 is linked for data exchange with ADADP unit 52. Sensor-stimulator unit 50 and ADADP unit 52 are illustrated schematically in FIG. 3, and are not shown in contact with a subject, a neurovascular head model, or any neurovascular substrate. But in actual use, sensor-stimulator unit 50 would be selectively placed in communication with a neurovascular substrate (not pictured). Once in place, transcranial direct current stimulation (tDCS) is generated, and is sent from ADADP unit 52 to sensor-stimulator unit 50, as represented by pathway 54. Within sensor-stimulator unit 50 is a selected array of electrodes, NIRS detectors, and other electrical components. With respect to NIRS, a source/detector pair is used, where the detector measures changes in intensity of NIR light provided by the source. From the changes in NIR light intensities, it is possible to calculate concentrations of light absorbers in the tissue, such as hemoglobin and oxygenated hemoglobin. In the example of FIG. 3, sensor-stimulator unit 50 includes cathode 60, anode 65, NIRS detector 68, and NIRS sources 70, as arrayed in the figure. Also included are EEG ring-electrodes 72, and other return electrodes 74, 76 and 78 for steering current [11]. After initiation of tDCS and activation of NIRS sources 70, the evoked response in the substrate (not pictured) is conveyed to ADADP unit 52, as represented by pathway 80.

The stimulation electrode array incorporated in sensor-stimulator unit 50 injects energy non-invasively in the form of electric field called transcranial direct current stimulation (tDCS), as represented by pathway 54. The stimulation electrode array in the sensor-stimulator unit is used to orient the electric field by coordinating the current injected via multiple electrodes, 60, 65, 74, 76, and 78. This process is called current steering as mentioned above. Current steering is undertaken when the system is in use in order to target neurovascular substrate (not pictured). Also, optical stimulation is delivered by NIRS sources 70 to target a neurovascular substrate such as that pictured in FIG. 2. The recording sensor array, which includes NIRS detector 68 and EEG ring electrodes 72, measures the emanating energy 80, evoked in the form of electric field in response to the stimulation. This single sensor-stimulator unit (NIRS-EEG/tDCS unit) 50 can be arrayed to target a ROI of cerebral neurovascular substrate with multi-unit recordings. NIRS source 70 and NIRS detector 68 use a multi-distance approach to differentiate the attenuation of light by the skull and the cerebral tissue of a subject (not pictured). The NIRS source 70 closer to the NIRS detector 68 primarily registers the attenuation of light by scalp (systemic component) while the NIRS source 71 further from the NIRS detector 68 registers the attenuation of light by cerebral tissue (referred to herein as the functional component) as well as a systemic component, generated by the blood vessels in the skin or scalp. The closer NIRS source-detector pair and the distant NIRS source-detector pair are alternately recorded where the systemic component is identified by using different intensity of tDCS. Lower currents will only stimulate the scalp and therefore result in primarily systemic component that will be reflected in both the closer as well as the distant NIRS source-detector pair. As the current is increased, the stimulation of brain tissue will occur resulting in functional component that will be captured primarily by the distant NIRS source-detector pair and the closer NIRS source-detector pair recordings shouldn't change. Therefore, the known signals generated by the scalp can be "removed", for example, by subtracting using a regression model. This calibration performed by sensor-stimulator unit 50 will separate the functional component from the systemic component, thereby generating the functional component that we are most interested in. Based on the application to record from single or multiple brain regions, a single wavelength and a fixed distance between the electrode, or multiple wavelengths and a fixed distance or a single wavelength and multiple inter-electrode distances may be used to detect the variations in the intensity, phase and modulation of the signal.

Figure 4:
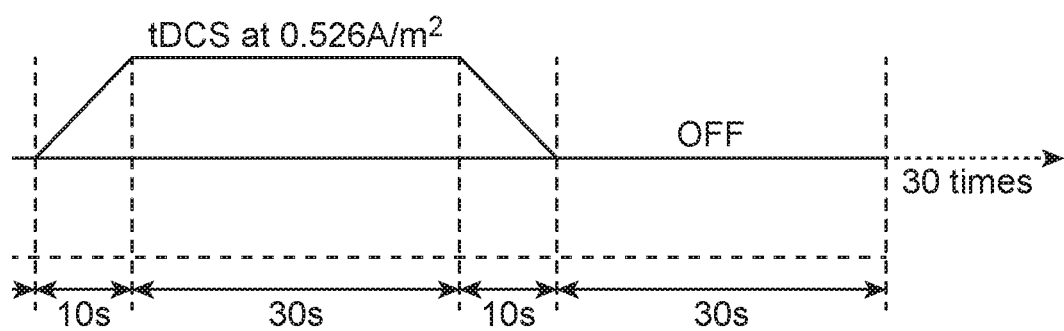
FIG. 4 is a graph illustrating a step of a method according to the invention.

In the example of FIG. 3, tDCS stimulus (54) consists of a ramp-up from 0 $A/m^2$ in 10 seconds to 0.526 $A/m^2$, steady state 0.526 $A/m^2$ for 30 seconds, and then ramp-down to 0 $A/m^2$ in 10 seconds, as illustrated in the graph of FIG. 4. In actual use, the evoked response is captured simultaneously with NIRS+EEG, represented by pathway 80, during tDCS (10+30+10 seconds in this illustrative example) as well as after tDCS (OFF state, 30 seconds in this illustrative example). Employing the system illustrated in FIG. 2 according the the foregoing steps would be expected to produce the spectrum illustrated in FIG. 1. However, other combinations of ramp up, duration and ramp down times are within the scope of the invention.

As mentioned above in relation to FIG. 2, an ADADP unit described in the present invention, in whole or in part, can be implemented on a computer system or network. A suitable computer system includes at least a processor and memory; optionally, a computer-readable medium that stores computer code for execution by the processor. Once the code is executed, the computer system carries out the described methodology. In this regard, a "processor" is an electronic circuit that can execute computer programs. Suitable processors are exemplified by but are not limited to central processing units, microprocessors, graphic processing units, digital signal processors, network processors, front end processors, coprocessors, data processors and audio processors. The term "memory" connotes an electrical device that stores data for retrieval. In some embodiments, therefore, a suitable memory is a computer unit that preserves data and assists computation. More generally, suitable methods and devices for providing the requisite network data transmission are known. Also contemplated is a non-transitory computer readable medium that includes executable code for carrying out the described methodology. In certain embodiments, the medium further contains data or databases needed for such methodology.

Figure 5:
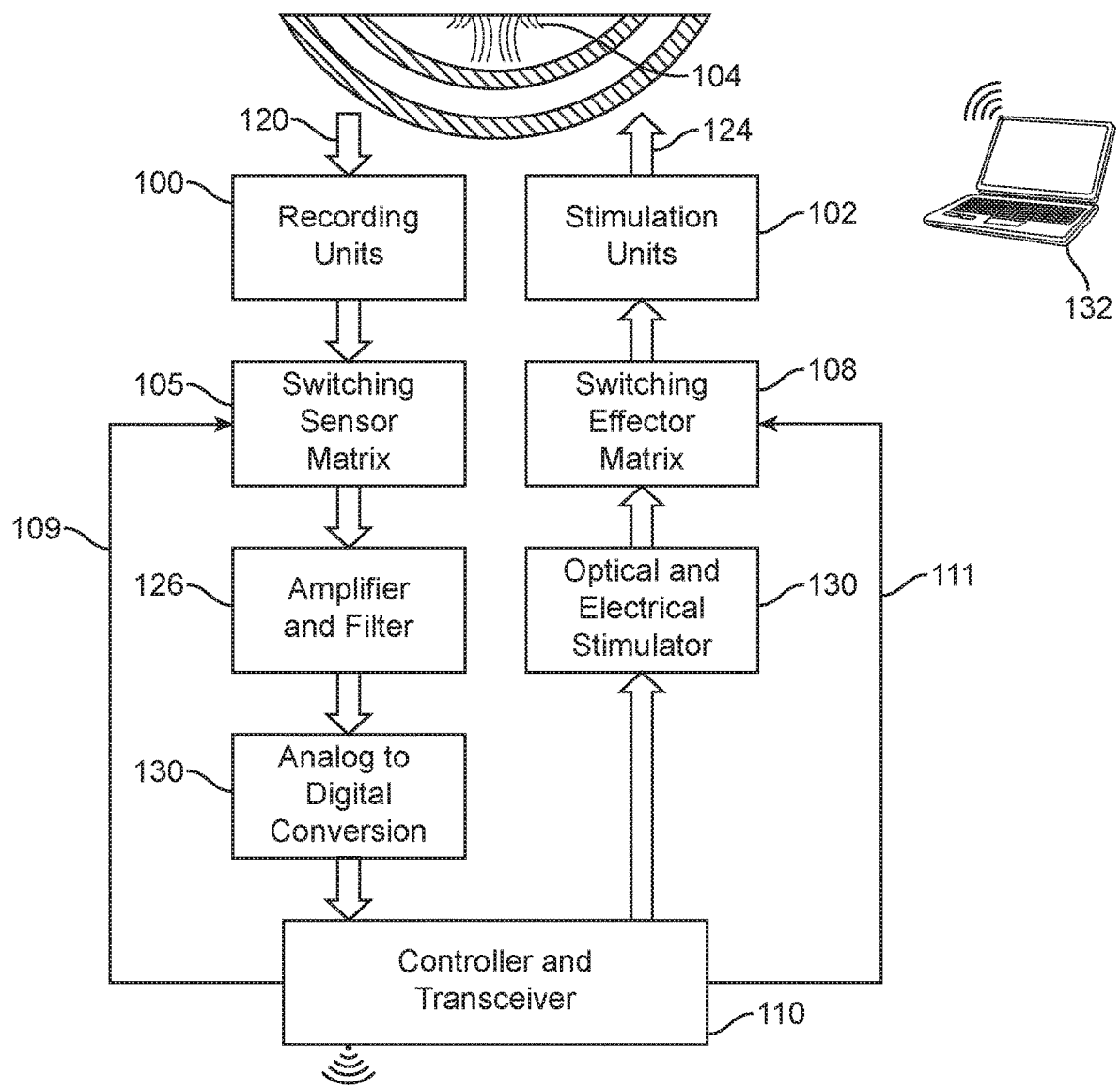
FIG. 5 is a schematic illustration of a system and method according to the invention.

FIG. 5 schematically illustrates an alternative embodiment according to the invention, by illustrating an exemplary function pathway of the embodiment. In the embodiment illustrated in FIG. 5, a set of recording sensors 100 and a set of stimulation units 102 are in communication with a neurovascular substrate 104. A set of recording sensors 100 can be selected by a switching sensor matrix 102. Similarly, a set of stimulation electrodes 120 can be activated by switching effector matrix 108. The controller and transceiver 110 controls the switching sensor matrix 106 according to arrow 109 to record emanating energy 120. Controller and transceiver 110 also controls switching effector matrix 108 (illustrated as arrow 111) to coordinate energy injection 124. In the example of FIG. 5, both energy injection 124 and emanating energy 120 are in the form of electric field and light. The optical and electrical stimulator 130 produces the required levels of electric field and light that the switching effector matrix 108 delivers spatially in an optimal manner to target a region of interest (ROI) of cerebral neurovascular substrate 104.

Optimal scalp placement of recording units 100 to target a ROI of cerebral neurovascular substrate 104 will result in the recording of emanating energy 120, and help determine if the ROI has a deficit. After recording of emanating energy 120, the signal can be amplified and filtered by amplifier and filter unit 126, and then converted to digital data by the analog to digital conversion unit 130. The digital data can then be transmitted wirelessly by controller and receiver unit 110 to base station 132 for multi-unit data storage and processing (as described above).

Figure 6:
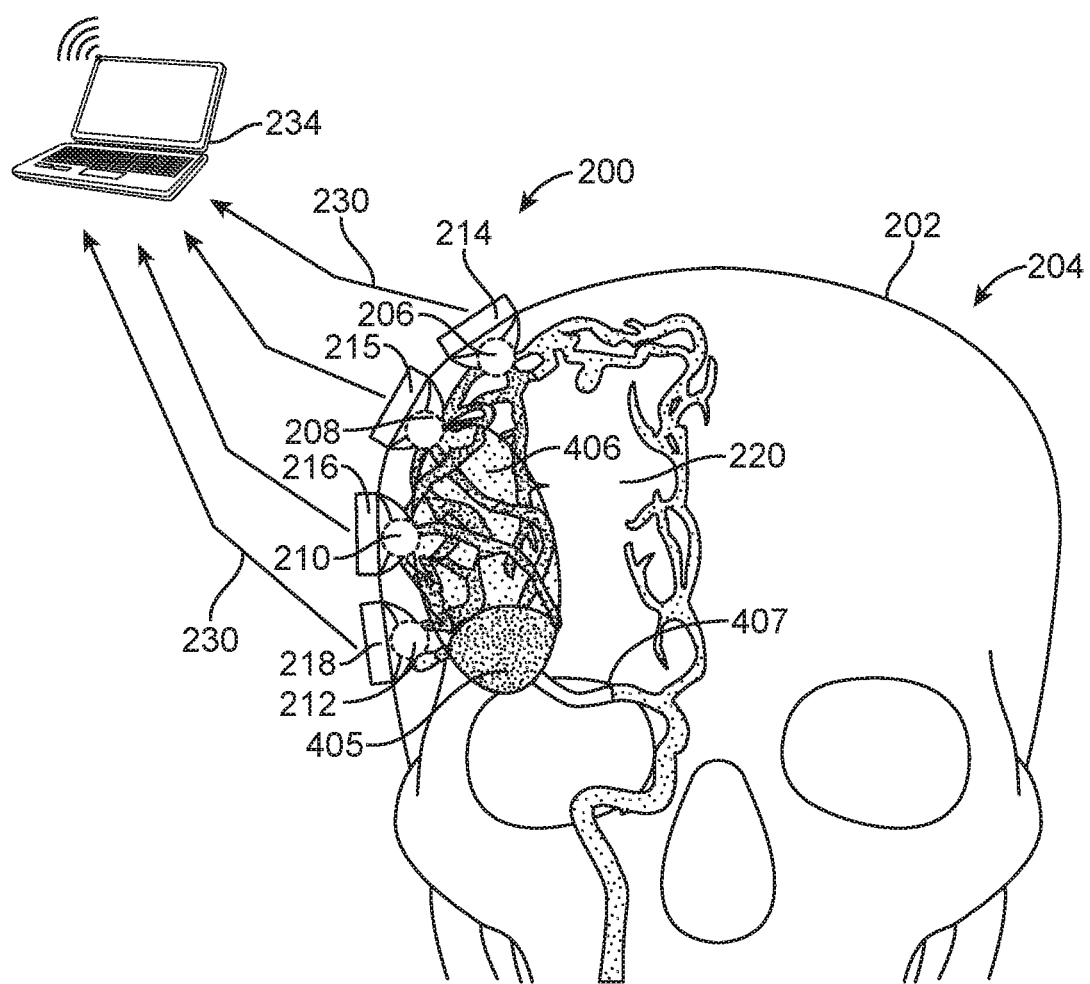
FIG. 6 is a schematic illustration of another embodiment of a system and method according to the invention.

FIG. 6 illustrates yet another alternative embodiment according to the invention. The embodiment of FIG. 6 is shown mounted on the scalp of a subject. More particularly, FIG. 6 illustrates an arrayed multiple sensor-stimulator unit 200. Multiple sensor-stimulator unit 200 may also be referred to as NIRS-EEG/tDCS unit 200. Multiple sensor-stimulator unit 200 includes individual units 214, 215, 216 and 218. A first sensor-stimulator unit 214 is mounted to scalp 202 of subject 204 according to known anatomical landmarks in order to probe a ROI 206 of neurovascular substrate 220. Similarly, sensor stimulator units 215, 216, and 218 are mounted to scalp 202 in order to probe ROIs 208, 210 and 212 respectively. ROIs 206, 208, 210 and 212 are suspected of having a deficit.

Sensor-stimulator units 214, 215, 216 and 218 inject energy in the form of NIRS and tDCS to ROIs 206, 208, 210 212 respectively. Contemporaneously, sensor-stimulator units 214, 215, 216 and 218 record the emanating energy as EEG and NIRS. The data is transmitted, (preferably wirelessly), as represented by arrows 230 to base station 234. Then, adaptive beamforming of the multi-unit recordings at base station 234 is performed. The term "beamforming" is intended to refer to a signal processing technique used in sensor arrays for directional signal transmission or reception. Beamforming may also be referred to as spatial filtering. In this example, beamforming is performed to iteratively estimate the three-dimensional (3D) location of ischemic core 405 and penumbra 406, which cannot be probed directly by sensor stimulator units 214, 215, 216 and 218.

In this illustrative example, the source of the abnormality is middle cerebral artery (MCA) occlusion 407 creating an ischemic core 405 and anterior cerebral artery (ACA) collateral flow creating a gradient of perfusion deficit in the penumbra 406. The assessable neurovascular substrates 206, 208, 210 and 212 that can be probed directly by the sensor-stimulator units 214, 215, 216 and 218 respectively are directly targeted by four sensor-stimulator units. Following adaptive beamforming performed at base station 234, in order to iteratively estimate the locations of ischemic core 405 and penumbra 406, sensor stimulator units 214, 215, 216 and 218 may be reconfigured based upon library data developed using a neurovascular head model and imaging techniques such as MRI.

Generative neurovascular head-model shows that even focal stimulation can evoke widespread response due to the connectivity of the neurovascular substrate that projects the 3D location of an ischemic core (405) as well as penumbra (406) to the recordings made by arrayed multiple sensor-stimulator unit (NIRS-EEG/tDCS unit) on the scalp. Here, underlying alterations of cortical activity induced via tDCS can be modeled with neuronal field/mass models [12]. In our prior work (neurovascular tissue probed by single NIRS-EEG/tDCS unit), we aimed to capture the origin of tDCS-induced local alterations in the electroencephalography (EEG) power spectrum using a thalamocortical neuronal mass models (NMM) [13]. We found that anodal tDCS enhances activity and excitability of the excitatory pyramidal neuron at a population level in a non-specific manner, and that μ-rhythm desynchronization is generated. The NMM for a single cortical source comprised of 4 neuronal subpopulations, excitatory pyramidal neurons (ePN), excitatory interneurons (eIN), slow inhibitory interneurons (siIN), and fast inhibitory interneurons (fiIN) [14]. The NMM for the cortical source was coupled with another representing the thalamus [15], which comprised of 2 neuronal subpopulations—an excitatory thalamocortical (eTCN) and an inhibitory reticular-thalamic (iRT). The basis of our cortical NMM was the Friston model [16] that emulated the activity of a cortical area using three neuronal subpopulations, ePN, eIN, and siIN. A population of ePN (output) cells received inputs from inhibitory and excitatory populations of interneurons via intrinsic connections (intrinsic connections are confined to the cortical sheet). An extrinsic thalamo-cortico-thalamic loop consisted of eTCN and iRT in the thalamic NMM [17]. Our lumped thalamo-cortico-thalamic network model can be used to simulate the subject-specific EEG power spectral density changes during tDCS [13] by modifying the model parameters (e.g., average gain of synapses, their time constants) [14]. Specifically, each neuronal subpopulation had an average membrane potential $V_i$(i=ePN, eIN, siIN, eTCN, iRT), which served as input for a sigmoid function that converted it into average density of spikes, $Z_i$(i=ePN, eIN, siIN, eTCN, iRT), fired by the respective neuronal subpopulation [16]. This output from neuronal subpopulations entered synapses (excitatory or inhibitory) via a second order linear function. The second order differential equation representing the synapses was described by a lumped gain, $G_i$, and a lumped time constant, $\tau_i$, $$\ddot{Y}_i(t) = G_i \frac{1}{\tau_i} Z_i(t) - 2 \frac{1}{\tau_i} \dot{Y}_i(t) - \left(\frac{1}{\tau_i}\right)^2 Y_i(t)$$

where $Y_i$(i=ePN, eIN, eTCN, iRT) represented the postsynaptic membrane potentials, which can be excitatory or inhibitory. Interactions among neuronal subpopulations were modeled via connectivity constants, $C_{ij}$(i,j=ePN, eIN, siIN, eTCN, iRT), which scaled the postsynaptic membrane potentials, $Y_i$, from various synaptic inputs to produce alterations of the lumped membrane potential, $V_i$, at the soma. Therefore, membrane potential alterations of ePN represented synaptic inputs from all interconnected neuronal subpopulations. The membrane potential alterations of ePN was used as an estimator of the EEG power spectral density in our case, based on prior work [14], however, transmembrane current is a more reliable estimator. [18] A Gaussian white noise input, I(t), with a mean, m(t), and variance, $\sigma^2$, was provided to the ePN subpopulation. The average density of spikes, $Z_i$, arriving as presynaptic input was transformed into average postsynaptic membrane potentials, $Y_i$. This was modeled by convolving $Z_i$ with the synaptic impulse response function (sIRF) of the dendritic tree.

$$Y_i(t) = sIRF_i(t) \otimes Z_i(t)$$

$$sIRF_i(t) = G_i \frac{1}{\tau_i} t \exp\left(-\frac{t}{\tau_i}\right)$$

The parameter, $G_i$, which tuned the maximum amplitude of the postsynaptic membrane potential and the parameter, $\tau_i$, was a a lumped representation of the sum of the rate constants of the membrane and other spatially distributed delays in the dendritic tree.

The excitation versus inhibition effects of acute tDCS on the population kinetics can produce a whole spectrum of EEG signals within the oscillatory regime of a neuronal mass model [19] where connectivity between neuronal masses, e.g. 401, 402, 403, 404 illustrated in FIG. 6, will be important. Here, the effects on the population kinetics will depend on the direction of cortical current flow determining the relative influence of acute tDCS on the cellular targets responsible for modulation of synaptic efficacy, which are primarily somata and axon terminals [20]. Not all neuronal tissue will be equally affected by a given stimulation protocol which may distinctly affect neuronal populations/neuronal compartments. Therefore, current steering within the NIRS-EEG/tDCS unit is necessary to target different neuronal tissue [11] to probe them. This needs a 3-dimensional multi-shell generative forward head-model for simulating tDCS and its EEG response, e.g. electric field calculations using finite element methods [21], as described above in relation to FIG. 2.

During short-duration (30 seconds) tDCS that doesn't cause neuroplastic changes, neurovascular reactivity (NVR) can be measured as the change in neuronal activity (captured with EEG) in conjunction with hemodynamics in relation to energy injection through tDCS. The complex path from the tDCS-induced change of the synaptic transmembrane current, u(t) (only excitatory effects considered here) [12] to a change in the concentration of multiple vasoactive agents (such as NO, potassium ions, adenosine), represented by a single vascular flow-inducing vasoactive signal, s, can be captured by a first-order Friston's model [22].

$$\dot{s} = \varepsilon u(t) - k_s s - g_f(f-1)$$

where f denotes CBF normalized by its baseline value, $\varepsilon$ is the neuronal efficacy, $k_s$ is the rate constant for signal decay, and $g_f$ is the gain constant for an auto-regulatory feedback term that drives the CBF back to its baseline value (at steady state: $\dot{s}=0$, s=0 and $u(t)=g_f(f-1)/\varepsilon$, i.e., synaptic transmembrane current correlated with baseline-normalized CBF at steady state).

In fact, the intermediate vasoactive agents (such as NO) and metabolic pathways of oxygen utilization (such as cytochrome c oxidase) can be selectively stimulated optically thereby facilitating system identification of the NVU. For example, cytochrome c oxidase (Cox) is the primary photoacceptor for the red-NIR range between 630 and 900 nm [23] and either visible (514.5 nm) or long wavelength ultra-violet (lambda=366 nm) light to influence the localized production or release of NO [24]. The released vasoactive signal, s, changes the compliance, C, of the vasculature approximated by first-order kinetics, leading to changes in its representative radius, R, that can be captured by a nonlinear compliance model [25]. The photons in the near-infrared (NIR) spectral range (650-950 nm) are able to penetrate human tissue. NIR wavelengths can be selected such that the change in concentration of oxy-hemoglobin (HbO2) and deoxy-hemoglobin (Hb) in the brain tissue can be detected. NIRS instrumentation works on different measuring principles, e.g., continuous wave (CW), frequency domain (FD), and time domain (TD). Absolute concentration measurements may be possible with more expensive TD and FD techniques [26], but a relative change in HbO2 and Hb in response to tDCS is all that is necessary for data fitting to estimate neurovascular coupling rather than to quantify the hemodynamic response in absolute terms. For ease in NIRS data fitting, the nonlinear compliance model was linearized about an equilibrium point $C_M$, and the radius, R, was approximated as, $$\dot{C} = s$$

$$R = R_{max}(1 - a_1 \exp(-a_2 C_M))$$

where $R_{max}$ is the maximum radius, and $a_1$ and $a_2$ are constants. The CBF, i.e., the volume of blood that flows through a unit volume of tissue in a given time unit can be approximated using the Ohmic equation, $$CBF = K(P_a - P_v)R^\gamma$$

where $P_a$ and $P_v$ are arterial and venous blood pressures, K is a constant of proportionality, and the exponent $\gamma$ is 2 for plug-flow and 4 for laminar flow. Anodal tDCS is assumed to change CBF via synaptic transmembrane current, u(t), leading to changes only in R and not in blood pressure difference ($P_a - P_v$). Under this simplifying assumption, the baseline-normalized CBF, f, can be approximated as $$f = \left(\frac{R}{R_0}\right)^\gamma$$

where $R_0$ is the radius of tissue vasculature at baseline. Since NIRS measures changes in tissue oxy-(HbO2), and deoxy-(Hb) hemoglobin concentration, these need to be approximated based on f. So a third hemodynamic variable, Hbt, was derived as the sum of HbO2 and Hb concentrations, which is considered a good indicator of variations of regional cerebral blood volume, $Vol_{blood}$ [27]. Under the assumption that the tissue vasculature has a volume, $V_{vasc}$, proportional to $R^2$ and haematocrit remains constant, the changes in tissue total (Hbt) hemoglobin concentration can be approximated as [28]

$$\frac{Vol_{vasc}}{Vol_{vasc,0}} = \frac{R^2}{R_0^2} \Rightarrow \frac{Vol_{blood}}{Vol_{blood,0}} = \frac{R^2}{R_0^2} \Rightarrow \frac{Hbt}{Hbt_0} = \frac{R^2}{R_0^2},$$

$$\therefore \text{haematocrit constant} \Rightarrow f = \left(\frac{Hbt}{Hbt_0}\right)^{\gamma/2}$$

The cerebral metabolic rate of oxygen, CMRO2 (i.e., oxygen consumption), is given by the difference of oxygen flowing into and out of the tissue [28]. Assuming that the arterial oxygen concentration, $C_A$, is unaffected by anodal tDCS [25], CMRO2 can be related to CBF as, $$CMRO2 = E \cdot C_A \cdot CBF \Rightarrow \frac{CMRO2}{CMRO2_0} = \frac{E(f, E_0)}{E_0} f$$

where E is the extraction fraction of oxygen ($E_0$ at baseline). CVR was defined as the ratio between fractional CBF chance and fractional CMRO2 change from baseline, $$CVR = \frac{CMRO2/CMRO2_0}{f} \Rightarrow CVR = \frac{E(f, E_0)}{E_0}.$$

The baseline-normalized CMRO2 (i.e. CVR·f) can be estimated from baseline-normalized tissue CBF (f), and deoxy-(Hb) and total (Hbt) hemoglobin concentration using the ratio method [28], $$\left(1 + \frac{CMRO2}{CMRO2_0}\right) = (1+f)\left(1 + \gamma_R \frac{Hb}{Hb_0}\right)\left(1 + \gamma_T \frac{Hbt}{Hbt_0}\right)^{-1} \Rightarrow (1 + CVR \cdot f) =$$

$$(1+f)\left(1 + \gamma_R \frac{Hb}{Hb_0}\right)\left(1 + \gamma_T \frac{Hbt}{Hbt_0}\right)^{-1} \Rightarrow \left(1 + CVR \cdot \left(\frac{Hbt}{Hbt_0}\right)^{\gamma/2}\right) =$$

$$\left(1 + \left(\frac{Hbt}{Hbt_0}\right)^{\gamma/2}\right)\left(1 + \gamma_R \frac{Hb}{Hb_0}\right)\left(1 + \gamma_T \frac{Hbt}{Hbt_0}\right)^{-1}$$

where the factors $\gamma_R \in [0.5, 1.5]$; $\gamma_T \in [0.5, 1.5]$ relate fractional hemoglobin changes in the venous compartment relative to those across all vascular components, and $SO2_0$ relates oxygen saturation at baseline of the venous compartment to $Hbt_0$ [28].

$$SO2_0 = \frac{HbO2_0}{Hb_0 + HbO2_0} \Rightarrow SO2_0 = \frac{Hbt_0 - Hb_0}{Hbt_0}.$$

In case of diffusion-limited oxygen delivery [29], oxygen consumption is limited by diffusion of oxygen from the vasculature, thus oxygen consumption is tightly coupled to induced blood flow [28] and the surface area of the vasculature (i.e. proportional to R). The generative forward head-model consisting of a network of neuronal mass model [13], each corresponding to a sensor-stimulator unit (e.g. 214, 215, 216, 218 illustrated in FIG. 6) relating anodal tDCS intensity (current density), σ(t), to tDCS-induced changes in synaptic transmembrane current, u(t) can be coupled with the neurovascular coupling model representing the hemodynamics (Hbt) response. Anodal tDCS, σ(t), at a single sensor-stimulator unit can effect a response at multiple sensor-stimulator units where deoxy-(Hb) is a byproduct of the consumption of oxygen delivered by oxy-(HbO2) hemoglobin that can be estimated using the cerebral metabolic rate of oxygen, CMRO2 (and $$\left(\text{and } CVR = \frac{E(f, E_0)}{E_0}\right)$$

[30]. Here, oxygen utilization during tDCS can be probed via the measurement of the oxidation state of cytochrome-c-oxidase using broadband NIRS [31]. Such an underlying physiological generative model will reduce systematic estimation errors, loss of robustness, and inaccuracies in localization of the ischemic core using multimodal multi-unit beamforming where inverse problem is ill-posed and prior information must be included to give a unique solution.

Figure 7:
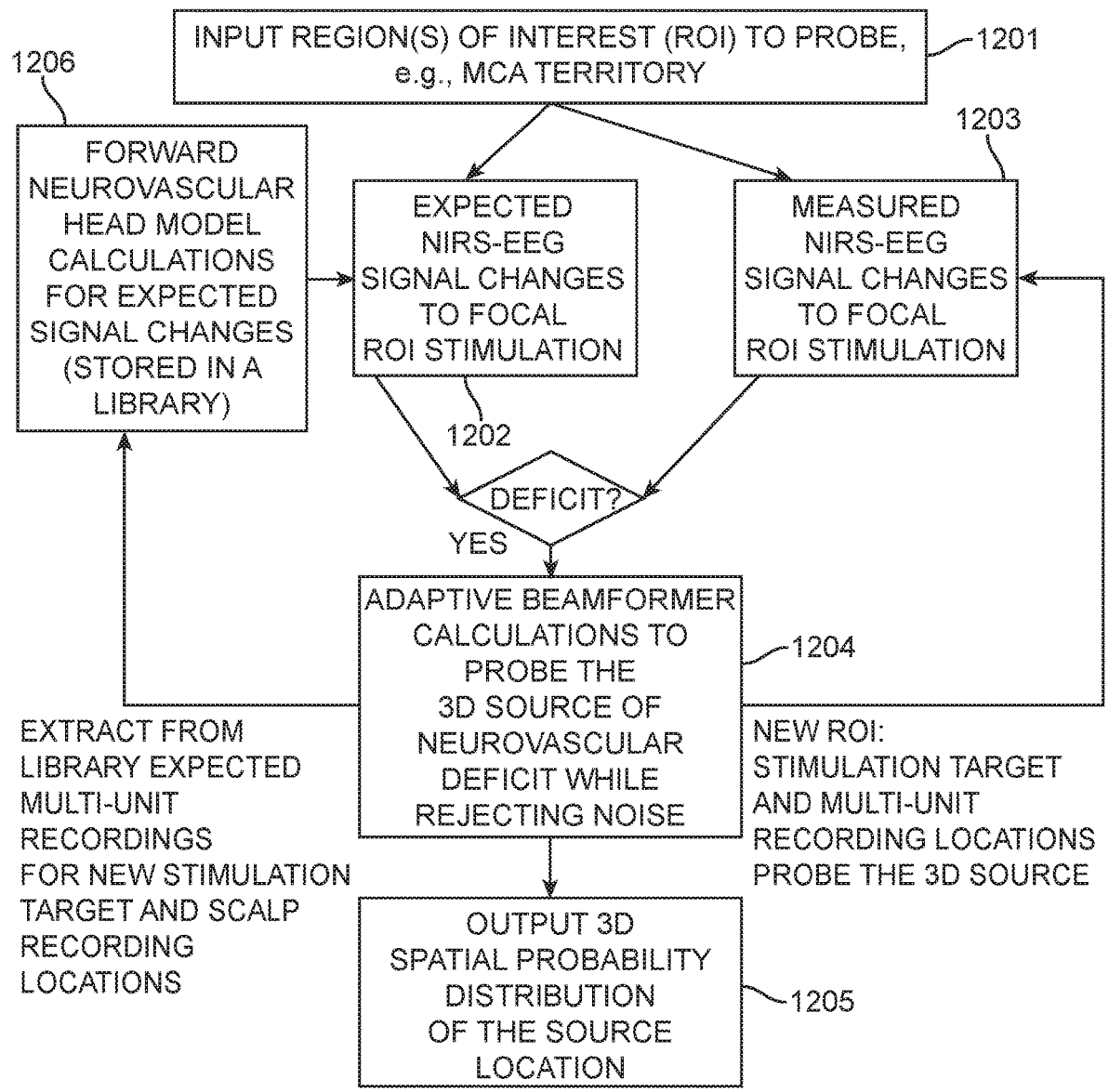
FIG. 7 is a flow diagram of the embodiment of the invention of FIG. 6.

Referring now to the embodiment having the adaptive beamforming operation sequence with arrayed multiple sensor-stimulator units (NIRS-EEG/tDCS units) 200 of FIG. 6, a flow chart is illustrated in FIG. 7. The clinician initializes the iteration with a region of interest (ROI) to probe, e.g. MCA territory (1201). In this example, a priori information is also provided in form of a library of forward calculations of neurovascular head model (1206) for expected signal alterations (1202) to a focal ROI stimulation at the scalp level. If the observed/measured signal alterations (1203) don't match the expected healthy signal alterations (1202) to a focal ROI stimulation, then there is an abnormality/deficit in the NVU. In an illustrative example, EEG-NIRS based monitoring of NVU under perturbation with tDCS [32], we present a black-box method for the assessment of neurovascular coupling using current source density (CSD) [33] and total hemoglobin concentration estimated from NIRS (Hbt) at the site of anodal tDCS (i.e. at the recording sensor (array) level). Empirical Mode Decomposition (EMD) of CSD and Hbt time series into a set of intrinsic mode functions (IMFs) is performed using Huang Hilbert Transform (HHT) [34]. Generally, the first IMF contains the highest frequency components and the oscillatory frequencies decrease with increasing IMF index. The IMFs for CSD are denoted as $CSD_i$ and IMFs for Hbt are denoted as $Hbt_i$.

The Hilbert transform of an IMF can be denoted as, $$H_{CSD,i}(t) = \frac{1}{\pi} P \int_{-\infty}^{\infty} \frac{CSD_i(\tau)}{t - \tau} d\tau \tag{1}$$

$$H_{Hbt,i}(t) = \frac{1}{\pi} P \int_{-\infty}^{\infty} \frac{Hbt_i(\tau)}{t - \tau} d\tau \tag{2}$$

where P is the Cauchy principal value. Then, the analytic signals are defined as, $$Z_{CSD,i}(t) = CSD_i(t) + iH_{CSD,i}(t) \tag{3}$$

$$Z_{Hbt,i}(t) = Hbt_i(t) + iH_{Hbt,i}(t) \tag{4}$$

The instantaneous amplitudes for the analytic signals can be determined as, $$A_{CSD,i}(t) = [CSD_i^2(t) + H_{CSD,i}^2(t)]^{1/2} \tag{5}$$

$$A_{Hbt,i}(t) = [Hbt_i^2(t) + H_{Hbt,i}^2(t)]^{1/2} \tag{6}$$

The instantaneous phases for the analytic signals can be determined as, $$\theta_{CSD,i}(t) = \arctan\left(\frac{H_{CSD,i}(t)}{CSD_i(t)}\right) \tag{7}$$

$$\theta_{Hbt,i}(t) = \arctan\left(\frac{H_{Hbt,i}(t)}{Hbt_i(t)}\right) \tag{8}$$

The instantaneous frequency for the analytic signals can be determined as, $$f_{CSD,i}(t) = \frac{1}{2\pi} \cdot \frac{d\theta_{CSD,i}(t)}{dt} \quad (9)$$

$$f_{Hbt,i}(t) = \frac{1}{2\pi} \cdot \frac{d\theta_{Hbt,i}(t)}{dt} \quad (10)$$

Only the IMFs that had instantaneous frequency less than 11.25 Hz for the whole signal duration were selected for comparison, i.e. cross-spectrum and coherence from 0.5 Hz-11.25 Hz.

The cross-spectrum and coherence between CSD and Hbt can be calculated based on instantaneous amplitude and phase. Here, we will follow a sliding window method where the average instantaneous frequency is first computed. Then, the cross-spectrum at time instant, t, is computed for frequency, $f_j$, from CSD and Hbt from $m^{th}$ and $n^{th}$ observation windows which have average instantaneous frequency closest to $f^j$, i.e., $$C_{f_j}(CSD,Hbt) = A_{CSD,m}(t) A_{Hbt,n}(t) e^{i[\theta_{CSD,m}(t) - \theta_{Hbt,n}(t)]} \quad (11)$$

$$C_{f_j}(Hbt,CSD) = A_{Hbt,m}(t) A_{CSD,n}(t) e^{i[\theta_{Hbt,m}(t) - \theta_{Hbt,n}(t)]} \quad (12)$$

Also, the coherence is computed as, $$Coh_{CSD \to Hbt, f_j} = \frac{\langle C_{f_j}(CSD, Hbt)^2 \rangle}{\langle [A_{CSD,m}(t) e^{i\theta_{CSD,m}(t)}]^2 \rangle \langle [A_{Hbt,n}(t) e^{i\theta_{Hbt,n}(t)}]^2 \rangle} \quad (13)$$

$$Coh_{Hbt \to CSD, f_j} = \frac{\langle C_{f_j}(Hbt, CSD)^2 \rangle}{\langle [A_{Hbt,m}(t) e^{i\theta_{Hbt,m}(t)}]^2 \rangle \langle [A_{CSD,n}(t) e^{i\theta_{CSD,n}(t)}]^2 \rangle} \quad (14)$$

where $\langle \rangle$ denotes averaging over multiple paired windows for the given frequency, $f_j$. Here, significant positive values point to a causal relation [35].

The neurovascular coupling (NVC) for the given frequency, $f_j$ can be estimated from cross-spectral power and coherence as, $$NVC(f_j) = \langle C_{f_j}(CSD,Hbt) \rangle Coh_{f_j} \quad (15)$$

From this NVC spectrogram using brain stimulation evoked neuronal and hemodynamic responses, the degree of NVC at a certain time can be assessed based on the sum of power in a frequency band of interest, e.g., Theta band or Alpha band [36]. Furthermore, such markers derived from NIRS-EEG/tDCS for neurovascular disorders need to be established first from population studies. Burst suppression, in which bursts of electrical activity alternate with periods of quiescence or suppression is a well-known, readily discernible EEG marker of profound brain inactivation and unconsciousness. This pattern is commonly maintained when anesthetics are administered to produce a medically-induced coma for cerebral protection in patients suffering from brain injuries or to arrest brain activity in patients having uncontrollable seizures. Such coma may be required for several hours or days, where drug infusion rates can be managed by a closed-loop controlled based on NIRS-EEG feedback of burst suppression. Moreover, such markers derived from NIRS-EEG may be used for controlled reperfusion in acute stroke [37].

In case of an abnormality/deficit at the recording sensor (array) level, we present a Bayesian Inversion Approach for adaptive beamformer calculations (1204) to estimate the source of abnormality/deficit where simplest a priori assumption is the Minimum Norm Model (MNM). In this illustrative example using multiple sensor-stimulator unit (NIRS-EEG/tDCS unit), MNM estimates a source distribution that minimizes the error between the simulated 2D NIRS-EEG scalp data generated from the modeled sources (1202) and the observed 2D NIRS-EEG scalp data (1203), whilst simultaneously minimizing the overall source power. The probability of the sources of deficit can also be entered or else all sources can be equiprobable. Also, the candidate sources of deficit and their covariance prior can also be derived from the library (1206). The prior library (1206) can be based on an anatomical parcellation using clinical knowledge of common occlusion of vascular territories from offline running forward generative head model fitted to conventional neuroimaging data from stratified patient population studies. Here, the temporal constraint is imposed by the underlying physiological generative model (1206). For solving the inverse problem, well accepted Variational Bayes (VB) approach with Laplace approximation [38] can be used. Specifically, Automatic Relevance Determination (ARD) [39] method can be applied for automatic selection of multiple sources. ARD iterative selection process of the active priors can be performed reconfiguring a multiple sensor-stimulator unit (NIRS-EEG/tDCS unit) such as unit 200 of FIG. 6 in the iterative loop acquiring new data for a better estimate of the source location. The hyperparameters connected to the priors are iteratively updated using a Restricted Maximum Likelihood (ReML) routine [38] where free energy is the objective function of ReML, providing an approximation to the model evidence. ARD assumes a large number of putative sources and eliminates those that prove irrelevant for data explanation. ARD pruning also takes care of the noise where the sources lie outside of the headspace. After ARD pruning within a certain threshold, the remaining (deficient) sources and their 3D spatial probability distribution can be shown as the output (1205).

As an example of a simple embodiment using Kalman filter, we assume that the healthy neurovascular dynamics can be described by a discrete time linear model that is applicable to the superficial source underlying the sensor-stimulation unit, i.e., each sensor-stimulation unit probe one source.

$$x_{k+1} = A x_k + w_k$$

$$y_k = C x_k + v_k$$

Where A, C are transition matrices of compatible dimensions, $x_k \in \Re^n$ is the state vector (representing NVU of the source), $y_k \in \Re^m$ is the output vector, $w_k \in \Re^n$ and $v_k \in \Re^m$ are the process and measurement noise vectors respectively. We also assume that the initial state vector and noise vector are multi-variate independently and identically distributed (i.i.d.) Gaussian random variables with initial state $x_0 \sim N(\bar{x}_0, P_0)$, process noise $w_k \sim N(0, Q)$, measurement noise $v_k \sim N(0, R_k)$ where covariance matrices $P_0$, Q, $R_k$ are symmetric positive definite matrices. Furthermore, we assume that $x_0$, $w_k$ and $v_k$ are mutually uncorrelated.

Here, most relevant sources for the region of interest can be fused probabilistically, i.e., each Kalman filter representing a neurovascular source ($x_{k|k}^{source}$ source→401,402,403, 404 214, 215, 216, 218 from FIG. 6) and their corresponding likelihood terms $$\left( \prod_{j=1}^{k} p(y_j | y_1 \ldots y_{j-1})^{source} \right)$$

can be combined in a probabilistic mixture of sources to represent the state of the NVU for the region of interest (i.e. the deficient part), $$x_{k|k} = \sum_{source=1}^{M} x_{k|k}^{source} \frac{\prod_{j=1}^{k} p(y_j | y_{1 \ldots j-1})^{source} p(\text{source})}{\sum_{source=1}^{M} \left( \prod_{j=1}^{k} p(y_j | y_{1 \ldots j-1})^{source} \right)}$$

$$p(y_k | y_{1 \ldots k-1}) = \frac{1}{(2\pi)^{m/2} |CP_{k|k-1} C^T + R_k|} e^{-\frac{1}{2} z_k^T (CP_{k|k-1} C^T + R_k) z_k}$$

The subjective prior information was captured by p(1). In the Kalman filters, the likelihood terms $$\left( \prod_{j=1}^{k} p(y_j | y_{1 \ldots j-1})^{source} \right)$$

captured the relevant objective information from the observations for each source. This objective information was probabilistically combined with the subjective information encapsulated in prior (p(source)). An 'argument of the minimum' test can be done for selecting the worst source ($d_k$), $$d_k = \arg\min_{source} \left( \frac{\prod_{j=1}^{k} p(y_j | y_{1 \ldots j-1})^{source} p(\text{source})}{\sum_{source=1}^{M} \left( \prod_{j=1}^{k} p(y_j | y_{1 \ldots j-1}) \text{source} \right)} \right)$$

$d_k$ worst fits healthy neurovascular dynamics and therefore will be a probable deficient source in neurovascular disorder. Here, for pruning out the healthy sources and to focus on deficient sources, an 'argument of the maximum' test can be done for selecting the best source ($b_k$), $$b_k = \arg\max_{source} \left( \frac{\prod_{j=1}^{k} p(y_j | y_{1 \ldots j-1})^{source} p(\text{source})}{\sum_{source=1}^{M} \left( \prod_{j=1}^{k} p(y_j | y_{1 \ldots j-1}) \text{source} \right)} \right)$$

$b_k$ fits healthy neurovascular dynamics well and therefore can be removed to focus on the deficient sources. After $b_k$ is removed, the sensor-stimulation montage can be reconfigured (using forward head model calculations) to optimally probe the remaining probable deficient sources and this can be iterated until below threshold likelihood is reached on all the remaining sources $$\left( \left( \frac{\prod_{j=1}^{k} p(y_j | y_{1 \ldots j-1})^{source} p(\text{source})}{\sum_{source=1}^{M} \left( \prod_{j=1}^{k} p(y_j | y_{1 \ldots j-1}) \text{source} \right)} \right) \right)$$

that are supposed to be deficient.

Figure 8:
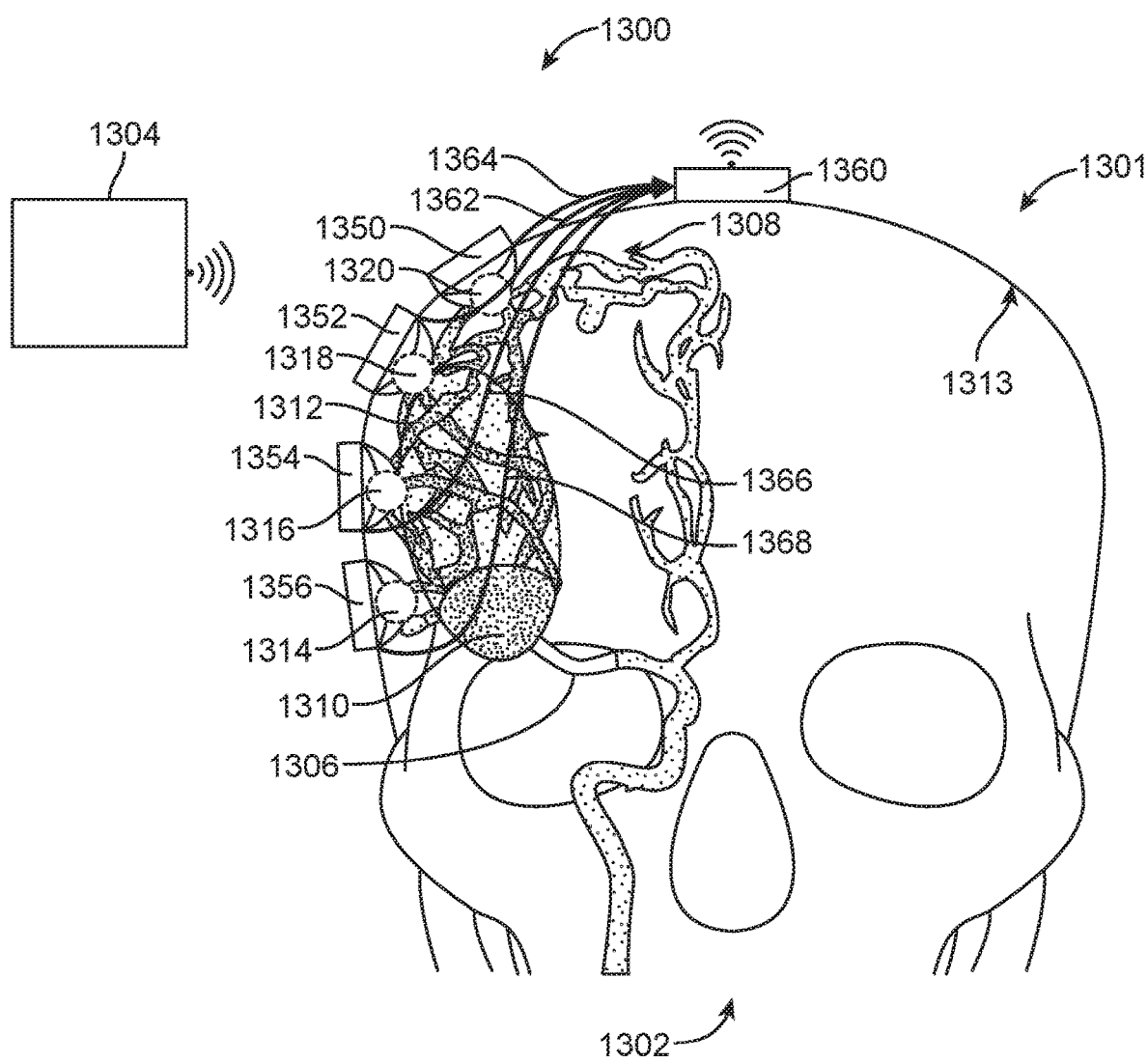
FIG. 8 is a schematic illustration of yet another embodiment of a system and method according to the invention.

FIG. 8 illustrates yet another embodiment according to the invention. The embodiment of FIG. 8 employs the same general principles and mathematical model fitted to capture the transfer function between hemodynamic reactivity and neuronal reactivity to brain stimulation of the foregoing examples. In the example of FIG. 8, system 1300 includes head unit 1301 disposed on the head of subject 1302. Head unit 1301 is in (preferably wireless) communication with base station 1304. Base station 1304 in this example is a hand held computer, such as a smart phone, tablet, laptop, or other similar portable computing device.

Subject 1302 in this example is experiencing a middle cerebral artery (MCA) occlusion 1306. As a consequence of MCA occlusion 1306, subject 1302 is also experiencing anterior cerebral artery (ACA) collateral blood flow (1308). In addition, MCA occlusion 1306 and ACA collateral blood flow 1308 have created ischemic core 1310 and penumbra 1312. A clinician has identified regions of interest (ROIs) 1314, 1316, 1318, and 1320. ROIs 1314, 1316, 1318, and 1320 will be targeted for local perturbation with tDCS with simultaneous NIRS+EEG neuroimaging in order to estimate the location of ischemic core 1310 and penumbra 1312.

Head unit 1301 includes cap 1313, worn over the head of subject 1302. Cap 1313 has NIRS-EEG/tDCS units 1350, 1352, 1354 and 1356 strategically mounted thereupon. NIRS-EEG/tDCS units 1350, 1352, 1354 and 1356 may include a cathode, an anode, NIRS detectors, NIRs sources, EEG electrodes and other return electrodes for current steering (not pictured). The foregoing components may be arrayed in a manner similar to the configuration illustrated in FIG. 3 and described above. In any event, the components are configured to deliver tDCS to regions of interest 1314, 1316, 1318 and 1320, while simultaneously recording the effects of the stimulus via NIRS+EEG.

NIRS-EEG/tDCS units 1350, 1352, 1354 and 1356 are connected to transceiver 1360 via wires 1362, 1364, 1366, and 1368 respectively. Wires 1362, 1364, 1366 and 1368 relay data from the NIRS-EEG/tDCS units to transceiver 1360. Transceiver 1360 transmits data to, and receives data from base station 1304. Base station 1304 performs processing according to mathematical models fitted to capture the transfer function between hemodynamic reactivity and neuronal reactivity to brain stimulation, and iteratively steers current from the NIRS-EEG/tDCS units in order to better estimate the location of penumbra 1312, ischemic core 1310, and MCA occlusion 1306.

Figure 9:
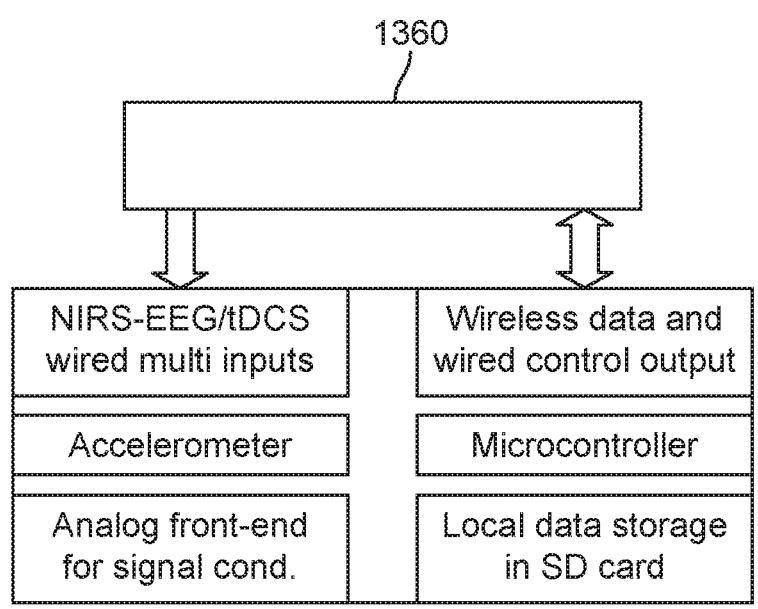
FIG. 9 is a flow diagram illustrating the function of a component of the embodiment of FIG. 8.

The functions of head-mounted transceiver 1360 are illustrated in FIG. 9. Transceiver 1360 receives multiple inputs from NIRS-EEG/tDCS units, which are connected by wire to transceiver 1360. These inputs as well as accelerometer recordings go to the Analog front-end for signal conditioning. Then the digital signal is sampled by the Microcontroller, then analyzed before being stored locally in SD card as well as sent wirelessly to the Base station 1304. The Microcontroller can also receive control signals wirelessly to the Base station 1304 and send control signals to the wired NIRS-EEG/tDCS units. Wireless data is transmitted and received by the transceiver from the base station 1304 and wired control output is sent to the NIRS-EEG/tDCS units. Base station 1304 includes a personal computer or a hand-held computed (not pictured). Local data storage within base station may be performed by a hard drive, secure digital (SD) card, or any device capable of storing memory. Base station 1304 includes a suitable computer system includes at least a processor and memory; optionally, a computer-readable medium that stores computer code for execution by the processor. Once the code is executed, the computer system carries out the described methodology. In this regard, a "processor" is an electronic circuit that can execute computer programs. Suitable processors are exemplified by but are not limited to central processing units, microprocessors, graphic processing units, digital signal processors, network processors, front end processors, coprocessors, data processors and audio processors. The term "memory" connotes an electrical device that stores data for retrieval. In some embodiments, therefore, a suitable memory is a computer unit that preserves data and assists computation. More generally, suitable methods and devices for providing the requisite network data transmission are known. Also contemplated is a non-transitory computer readable medium that includes executable code for carrying out the described methodology. In certain embodiments, the medium further contains data or databases needed for such methodology.

The advantages of the present invention include, without limitation, a device consisting of hardware and software that can initialize stimulation and recording of cerebral neurovascular substrate to assess the functionality of neurovascular unit and then adapt stimulation and recording to identify the source of any deficit. While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiments, and examples, but by all the embodiments falling within the scope of the invention.

What is claimed is:

1. A system for detecting a deficit in neurovascular function of the cerebral tissue of a subject, the system comprising:
   a source of perturbation energy for non-invasive perturbation of the cerebral tissue;
   a source of energy for measuring the hemodynamic response of the cerebral tissue to the perturbation;
   a first sensor coupled to the source of energy for measuring the hemodynamic response of the cerebral tissue to the perturbation, the first sensor configured to detect and record the hemodynamic response of the cerebral tissue to the perturbation; and
   a second sensor for measuring the neuronal response of the cerebral tissue to the perturbation, the second sensor configured to detect and record the neuronal response;
   wherein the source of perturbation energy, the source of energy for measuring the hemodynamic response of the cerebral tissue, the first sensor, and the second sensor are arrayed in a sensor-stimulator unit, and the system comprises a plurality of sensor-stimulator units;
   wherein the system further comprises a data acquisition and data processing unit in communication with the source of perturbation energy, the source of energy for measuring the hemodynamic response of the cerebral tissue, the first sensor, and the second sensor;
   wherein the data acquisition and data processing unit is configured to perform beamforming to locate the source of a deficit in neurovascular function by iteratively redirecting the delivery of energy and recording the response and by comparing the recordings of the successive perturbation and recording of each of the sensor-stimulator units.

2. The system according to claim 1, wherein the perturbation energy is light, electrical current, heat, sound, or vibration.

3. The system according to claim 1, wherein the source of energy for measuring the hemodynamic response of the cerebral tissue is light, sound, or vibration.

4. The system according to claim 1, wherein the perturbation energy is direct electrical current.

5. The system according to claim 1, wherein the source of energy for measuring the hemodynamic response of the cerebral tissue is light in the Near Infrared Spectrum range, and the sensor for measuring the hemodynamic response of the cerebral tissue is a Near Infrared detector.

6. The system according to claim 1, wherein the source of perturbation energy, the source of energy for measuring the hemodynamic response of the cerebral tissue, the first sensor, and the second sensor are selectively configured on the scalp of the subject in order to perturb the cerebral tissue in a region of interest, and to record the response of the tissue thereto.

7. The system according to claim 1, wherein the plurality of sensor-stimulator units is selectively placed on the scalp of the subject based upon a database of expected signal responses, the database obtained from healthy and patient experimental calibration data fitted to a three dimensional head model.

8. The system according to claim 1, wherein the plurality of sensor-stimulator units is selectively disposed in a cap for placement on the head of a subject, the sensor-stimulator units selectively disposed according to anatomical landmarks.

9. The system according to claim 1, wherein the data acquisition and data processing unit is configured to analyze the recorded responses to determine whether a neurovascular deficit exits in the cerebral tissue.

10. The system according to claim 9, wherein the data acquisition and data processing unit comprises a database obtained from healthy and patient experimental calibration data fitted to a three dimensional head model.

11. The system according to claim 9, wherein the data acquisition and data processing unit comprises an amplifier, a filter, and a digital converter, wherein the signal is amplified by the amplifier, filtered by the filter, and converted to digital data by the digital converter.

12. The system according to claim 9, wherein the data acquisition and data processing unit further comprises a controller and receiver unit and wherein digital data is transmitted wirelessly between (1) the controller and receiver unit and (2) a base station.

13. The system according to claim 9, wherein the data acquisition and data processing unit is configured to selectively redirect the source of perturbation energy based upon the hemodynamic response and the neuronal response of the cerebral tissue to the perturbation.

14. The system according to claim 9, wherein the data acquisition and data processing unit is configured to employ a mathematical algorithm to locate the source of a deficit of neurovascular function.

15. The system according to claim 1, wherein the system further comprises:
- a first stimulation unit for delivery of perturbation energy;
- a first recording unit for detecting and recording energy the hemodynamic response and the neuronal response of the cerebral tissue in response to the perturbation energy; and
- a controller and transceiver in communication with said first stimulation unit and said first recording unit.

16. The system according to claim 15, said system further comprising a switching sensor matrix, an amplifier, and a filter, and an analog to digital conversion unit in communication from said first recording unit to said controller and transceiver.

17. The system according to claim 15, said system further comprising an optical and electrical stimulator and a switching effector matrix in communication from said controller and transceiver to said first stimulation unit.

18. The system according to claim 1, wherein the second sensor measures the level of oxygenation of the blood, and wherein the data acquisition and data processing unit is configured to perform mathematical analysis that relates the level of oxygenation of the blood and the neuronal response.

19. The system according to claim 1, wherein the system further comprises a second source of energy for measuring the hemodynamic response, wherein the first source for measuring the hemodynamic response is disposed in a first proximity to the first sensor, and the second source of energy is disposed in a second proximity to the first sensor, wherein the second proximity is further from the first sensor than the first proximity.

20. A system for detecting a deficit in neurovascular function of the cerebral tissue of a subject, the system comprising:
- a source of perturbation energy for non-invasive perturbation of the cerebral tissue;
- a source of energy for measuring the hemodynamic response of the cerebral tissue to the perturbation; and
- a first sensor coupled to the source of energy for measuring the hemodynamic response of the cerebral tissue to the perturbation, the first sensor configured to detect and record the hemodynamic response of the cerebral tissue to the perturbation;
- wherein the source of perturbation energy, the source of energy for measuring the hemodynamic response of the cerebral tissue, the first sensor, and the second sensor are arrayed in a sensor-stimulator unit, and the system comprises a plurality of sensor-stimulator units;
- wherein the system further comprises a data acquisition and data processing unit in communication with the source of perturbation energy, the source of energy for measuring the hemodynamic response of the cerebral tissue, the first sensor, and the second sensor;
- wherein the data acquisition and data processing unit is configured to perform beamforming to locate the source of a deficit in neurovascular function by iteratively redirecting the delivery of energy and recording the response and by comparing the recordings of the successive perturbation and recording of each of the sensor-stimulator units.

21. A system for detecting a deficit in neurovascular function of the cerebral tissue of a subject, the system comprising:
- a source of perturbation energy for non-invasive perturbation of the cerebral tissue;
- a source of energy for measuring the hemodynamic response of the cerebral tissue to the perturbation; and
- a first sensor for measuring the neuronal response of the cerebral tissue to the perturbation, the first sensor configured to detect and record the neuronal response;
- wherein the source of perturbation energy, the source of energy for measuring the hemodynamic response of the cerebral tissue, the first sensor, and the second sensor are arrayed in a sensor-stimulator unit, and the system comprises a plurality of sensor-stimulator units;
- wherein the system further comprises a data acquisition and data processing unit in communication with the source of perturbation energy, the source of energy for measuring the hemodynamic response of the cerebral tissue, the first sensor, and the second sensor;
- wherein the data acquisition and data processing unit is configured to perform beamforming to locate the source of a deficit in neurovascular function by iteratively redirecting the delivery of energy and recording the response and by comparing the recordings of the successive perturbation and recording of each of the sensor-stimulator units.

\* \* \* \* \*